United States Patent
Quagliano

(10) Patent No.: US 11,529,429 B2
(45) Date of Patent: *Dec. 20, 2022

(54) LIQUID VEHICLE FOR ENTEROGRAPHY EXAMINATION

(71) Applicant: Peter Quagliano, Richmond, VA (US)

(72) Inventor: Peter Quagliano, Richmond, VA (US)

(73) Assignee: BEEKLY CORPORATION, Bristol, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/450,507

(22) Filed: Mar. 6, 2017

(65) Prior Publication Data

US 2017/0173189 A1 Jun. 22, 2017

Related U.S. Application Data

(63) Continuation of application No. 14/174,126, filed on Feb. 6, 2014, now Pat. No. 9,585,973, which is a continuation-in-part of application No. 13/021,996, filed on Feb. 7, 2011, now Pat. No. 9,585,836, which is a continuation-in-part of application No. 12/478,794, filed on Jun. 5, 2009, now abandoned.

(60) Provisional application No. 61/058,955, filed on Jun. 5, 2008.

(51) Int. Cl.
| | |
|---|---|
| *A61K 49/04* | (2006.01) |
| *A61K 9/00* | (2006.01) |
| *A61K 47/26* | (2006.01) |
| *A61K 47/36* | (2006.01) |
| *A61K 9/08* | (2006.01) |
| *A61K 47/02* | (2006.01) |
| *A61K 47/12* | (2006.01) |
| *A61K 47/22* | (2006.01) |
| *A61K 47/18* | (2017.01) |

(52) U.S. Cl.
CPC ........ *A61K 49/0438* (2013.01); *A61K 9/0053* (2013.01); *A61K 9/0095* (2013.01); *A61K 9/08* (2013.01); *A61K 47/02* (2013.01); *A61K 47/12* (2013.01); *A61K 47/22* (2013.01); *A61K 47/36* (2013.01); *A61K 49/04* (2013.01); *A61K 47/183* (2013.01); *A61K 47/26* (2013.01)

(58) Field of Classification Search
CPC .............. A61K 49/0438; A61K 9/0053; A61K 9/0095; A61K 9/08; A61K 47/02; A61K 47/12; A61K 47/183; A61K 47/26; A61K 47/36

See application file for complete search history.

(56) References Cited

U.S. PATENT DOCUMENTS

| | | | | |
|---|---|---|---|---|
| 3,236,735 | A * | 2/1966 | Brown | A61K 49/0404 424/9.411 |
| 5,346,690 | A | 9/1994 | Gunderson et al. | |
| 7,427,391 | B2 * | 9/2008 | Lauenstein | A61K 47/36 424/9.1 |
| 7,498,018 | B2 * | 3/2009 | Williams, III | A61K 49/0404 424/9.1 |
| 2003/0113377 | A1 * | 6/2003 | Dobrozsi | A61K 9/0056 424/486 |
| 2004/0146461 | A1 | 7/2004 | Giuliano et al. | |
| 2005/0074405 | A1 * | 4/2005 | Williams, III | A61K 49/0404 424/9.3 |
| 2006/0286259 | A1 | 12/2006 | Hargreaves | |
| 2007/0036733 | A1 | 2/2007 | Spence | |
| 2007/0082025 | A1 * | 4/2007 | Catani | A61K 31/732 424/439 |

FOREIGN PATENT DOCUMENTS

CN 103190665 * 7/2013

OTHER PUBLICATIONS

Quagliano et al. Oral Contrast Agents for CT: A Taste Test Survey, Jmmwl of Compmer Assisted Tomogmphy 215):720-722 (Year: 1997).*
Barwal et al., Development and evaluation of dietetic bitter ground ready-to-serve drink, J Food Sci Technol 2005, 42(2), 202-205. (Year: 2005).*
Kuehle et al., Hydro-MRI of the Small Bowel: Effect of Contrast Volume, Timing of Contrast Administration, and Data Acquisition on Bowel Distention, AJR 2006; 187:W375-W385. (Year: 2006).*
Ajaj et al., Dose Optimization of Mannitol Solution for Small Bowel Distension in MRI, Journal of Magnetic Resonance imaging 20:648-653 (2004). (Year: 2004).*
Sieczkowska et al., Efficacy of 3% sorbitol solution in preparation to magnetic resonance enterography in children with inflammatory bowel disease, Post N Med 2016; XXIX(4): 217-221. (Year: 2016).*

(Continued)

*Primary Examiner* — Michael G. Hartley
*Assistant Examiner* — Jagadishwar R Samala
(74) *Attorney, Agent, or Firm* — McCarter & English, LLP

(57) ABSTRACT

The liquid vehicles can be used to create dilute solutions of water-soluble pharmaceutical or non-pharmaceutical oral contrast agents. The liquid vehicles are formulated to provide desired osmolalities, viscosities, pH, and taste masking capabilities to match the particular intentions of the user and to complement the inherent differences in the various oral contrast agents. The liquid vehicles comprise an aqueous medium, an osmotic agent to adjust osmolality, a buffering agent, a viscosity agent, and sweeteners and flavoring agents to improve palatability.

22 Claims, 6 Drawing Sheets

(56) References Cited

OTHER PUBLICATIONS

Negaard et al., A prospective randomized comparison between two MRI studies of the small bowel in Crohn's disease, the oral contrast method and MR enteroclysis, Eur Radiol (2007) 17: 2294-2301. (Year: 2007).*
Quagliano, Oral Contrast Agents for CT: A Taste Test Survey, Journal of Computer Assisted Tomography 21(5):720-722 (Year: 1997).*
NIH Library, Comparison of VoLumen and Breeza Oral Contrast Agents in Pediatric Patients, first poted Oct. 27, 2016. (Year: 2016).*
Breeza® Flavored Beverage for Neutral Abdominal / Pelvic Imaging 221 download online Sep. 10, 2020 (Year: 2020).*
BREEZA™ Flavored Beverage for Neutral Abdominal / Pelvic Maging, downloaded online Sep. 10, 2020 (Year: 2020).*
Tasty New Beverage for Natural Abdominal-Pelvic Imaging Encourages Patients, downloaded online Sep. 10, 2020 (Year: 2020).*
Quagliano et al., Oral Contrast Agents for CT: A Taste Test Survey; Journal of Computer Assisted Tomography, 21(5):720-722.
Kool-Aid liquid drink mix blue raspberry flavor document, downloaded online on Apr. 17, 2015.

* cited by examiner

LIQUID VEHICLE FOR ENTEROGRAPHY EXAMINATION

This application is a continuation of U.S. application Ser. No. 14/174,126, which is a continuation-in-part of U.S. application Ser. No. 13/021,996 filed on Feb. 7, 2011, which is a continuation-in-part of U.S. application Ser. No. 12/478,794 filed on Jun. 5, 2009, which claims priority under 35 U.S.C. § 119(e) to U.S. Provisional Application No. 61/058,955 filed on Jun. 5, 2008, the entire contents of which are hereby incorporated by reference.

FIELD OF THE INVENTION

The present invention relates in one aspect to a range of liquid vehicles that can be used to create varied concentrations of dilute solutions of water-soluble oral contrast agents. In another aspect, the liquid vehicle/oral contrast admixture is administered orally to patients for gastrointestinal tract opacification prior to computed tomography imaging (CT), magnetic resonance imaging (MR), or conventional radiographic imaging (X-ray). The range of vehicle formulations is adapted to provide a range of osmolalities, viscosities, pH/buffering capacities, and taste masking properties of the final admixture, providing the clinician (end-user) the ability to match the oral contrast agent with the appropriate liquid vehicle for the desired diagnostic imaging features/characteristics.

BACKGROUND OF THE INVENTION

There are a variety of imaging techniques that have been used to diagnose disease in humans. One of the first techniques employed was X-rays. In X-rays, the images of the patients' body reflect the different densities of body structures. To improve the diagnostic utility of this imaging technique, contrast agents are employed to increase the density difference between various structures, such as between the gastrointestinal tract and its surrounding tissues. Barium sulfate and iodinated contrast media are the two primary pharmaceutical oral contrast agents used for X-ray gastrointestinal studies to visualize the esophagus, stomach, small intestine, and large intestine. Likewise, these same contrast agents are used for X-ray-based CT images to improve visualization and distension of the gastrointestinal tract and to provide improved contrast between the gastrointestinal tract and the structures adjacent to it, such as the blood vessels and lymph nodes. Such gastrointestinal oral contrast agents increase the density inside the esophagus, stomach, small intestine, and large intestine, and allow differentiation of the gastrointestinal system from the surrounding structures. Such gastrointestinal oral contrast agents also distend the bowel lumen allowing better evaluation of bowel wall structures, including abnormalities such as wall thickening or luminal obstruction.

Magnetic resonance imaging is another imaging technique; however, unlike X-rays and CT, MR does not utilize ionizing radiation. MR employs a magnetic field, radiofrequency energy and magnetic field gradients to make images of the body. The contrast or signal intensity differences between tissues mainly reflect the T1 and T2 relaxation values and the proton densities of the tissues. Like CT, MR can make cross-sectional images of the body and it is desirable for many MR scans that a gastrointestinal contrast agent be administered to allow differentiation of the gastrointestinal system from the surrounding structures.

Opacification of the gastrointestinal tract is a routine part of patient preparation prior to CT examination of the abdomen and pelvis, because proper filling and distention of the bowel lumen with contrast medium facilitates identification of the normal and abnormal anatomy. For this reason, oral contrast agents are administered to the vast majority of patients undergoing CT scans of the abdomen and pelvis. Less commonly, oral contrast agents are administered to patients undergoing MR scans of the abdomen and pelvis.

The properties of an ideal oral contrast agent for CT or MR include the following: good taste and pleasing consistency; low cost; premixed with a long shelf life; predictable and dependable transit time; absence of side effects or allergic reaction; non-absorbable; chemically inert, lack of precipitation or loss of suspension; low incidence of streak or magnet-susceptibility artifacts; Hounsfield unit (HU) opacity (contrast density or degree of brightness) for CT, and either hyperintensity ("bright") or hypointensity ("dark") for MR, which allow easy differentiation of bowel loops from adjacent structures and also allow easy visualization of the contrast-enhanced bowel wall. Unfortunately, no single agent fulfills all of these criteria. For example, sometimes a clinician desires a fast transit time of the oral contrast agent through the bowel whereas at other times a slow transit time is desired. Sometimes a clinician desires a bright contrast agent (which appears as white on CT or MR), often termed a positive contrast agent. At other times the clinician may desire a neutral or dark contrast agent (which appears gray or black, respectively, on CT or MR), often termed a negative contrast agent.

The Hounsfield scale is a quantitative scale for describing radiodensity. The Hounsfield unit (HU) scale is a linear transformation of the original linear attenuation coefficient measurement in which the radiodensity of distilled water at standard pressure and temperature is defined as zero HU, while the radiodensity of air is defined as −1000 HU. For comparison, the HU of various body structures include fat at −120 HU, muscle at +40 HU, and compact bone at +1000 HU.

In the early 1980s, when CT scan imaging was first gaining widespread use, the first oral agents used were the ionic iodinated contrast agents, comprised of the iodine-containing salts sodium diatrizoate, meglumine diatrizoate, or mixtures thereof. One example of the ionic iodinated oral contrast agents is Gastrografin® (Bracco Diagnostics, Princeton, N.J.), which is composed of the iodine-containing salts meglumine diatrizoate and sodium diatrizoate. Pharmaceutical agents like Gastrografin® were already approved for oral use and were widely used in full strength concentration for diagnostic gastrointestinal radiology imaging. These products, as well as the newer non-ionic iodinated agent approved for oral administration in the United States (e.g., iohexol, trade name Omnipaque®, GE Healthcare, Princeton, N.J.), were too concentrated in the form supplied by the manufacturers to be used for gastrointestinal opacification during CT imaging. These products were, therefore, diluted with water or other beverage in order to be of the proper concentration for optimal CT scan imaging.

Similarly, the gadolinium-based oral contrast agents, such as gadopentetate dimeglumine, are too concentrated in the form supplied by the manufacturers to be used for gastrointestinal opacification during MR imaging. These products must be diluted with water or other beverage in order to be of the proper concentration for optimal gastrointestinal opacification during MR imaging.

In addition to the use of iodine-based agents, barium sulfate-based oral contrast agents for CT scan imaging were developed and perfected, and these products are used by many radiology imaging centers. There are currently various formulations of the barium sulfate oral contrast agents, each with its unique imaging characteristics. Formulations vary in terms of the degree of Hounsfield unit opacification (higher HU correlates with a greater degree of brightness, or whiteness, on the CT image), transit time through the bowel, viscosity, ability to distend bowel loops, and taste/palatability.

Iodinated contrast agents intended for oral administration prior to CT imaging are usually mixed with either water or a commercial, artificially-sweetened beverage such as Kool-Aid® (Kraft Foods North America, Rye Brook, N.Y.). The clinician is able to vary the initial HU opacification (contrast density) by altering the ratio of oral contrast agent to beverage diluent. The clinician is also able to vary the palatability by choosing different beverages for dilution.

The ionic (e.g., sodium diatrizoate and meglumine diatrizoate) iodinated contrast agents for CT, the non-ionic (e.g., iohexol) iodinated contrast agents for CT, and the gadolinium-based (e.g., gadopentetate dimeglumine) contrast agents for MR have inherent differences in their chemical and physical properties that result in clinical differences in their application to gastrointestinal tract imaging, as well as significant differences in their palatability.

There is, therefore, a need for a ready-mixed range of liquid dilution vehicles that allows the clinician to vary the osmolality of the administered oral contrast (which affects transit time through the bowel, oral contrast density, and bowel distension), to vary the viscosity of the administered oral contrast (which affects the transit time and the degree of bowel lumen distension), to vary the pH and buffering capacity of the administered oral contrast (which affects the chance of precipitation or denaturation of the oral contrast when exposed to the low pH environment of the stomach), and to vary the flavor/sweetness of the liquid vehicle to best mask the inherent palatability issues unique to the oral contrast agent utilized.

This range of liquid dilution vehicles allows the clinician to match the appropriate vehicle characteristics to the inherent differences in the imaging and chemical characteristics of the various oral contrast agents. Furthermore, the clinician can vary the liquid vehicle/oral contrast agent mixture and concentration to match the desired imaging characteristics for a particular patient's imaging scan.

The liquid vehicle of the invention is designed to be used only with water-soluble oral contrast agents such as the iodine-based and gadolinium-based agents. Non water-soluble oral contrast agents such as barium sulfate and bentonite are not properly suspended by the liquid vehicle and are not suitable for admixture with the liquid vehicle of the invention.

SUMMARY OF THE INVENTION

The present invention relates generally to a range of liquid vehicle formulations that have unique characteristics of osmolality, viscosity, pH/buffering capacity, and taste masking properties for use with oral contrast agents. The liquid vehicle formulations of the present invention provide the clinician with options regarding the choice of a liquid vehicle for preparation of dilute oral contrast agents for gastrointestinal tract opacification during CT, MR, and radiographic imaging. The liquid vehicle formulations comprise an agent to control the osmolality of the liquid vehicle formulations.

The liquid vehicle formulations may include other additives to achieve the desired properties and characteristics for use with oral contrasting agents. For example, the liquid vehicle formulations may contain viscosity agents, pH/buffering agents, palatability agents such as sweeteners, flavors or bitterness blockers, and other functional agents such as preservatives, coloring agents, defoaming or surfactant agents, and stability agents.

In accordance with one aspect, the present invention is directed to a liquid vehicle for enterography examination comprising a solution for oral administration prior to the enterography examination by computed tomography imaging or magnetic resonance imaging. The solution comprises (a) water, (b) about 3 grams/liter to about 8 grams/liter mannitol, (c) about 9.5 grams/liter to about 19.5 grams/liter sorbitol, (d) a viscosity agent including about 0.0001 grams/liter to about 8 grams/liter hydrocolloid gum in an amount such that the viscosity of the liquid vehicle is between 1 to 100 cps, (e) an additional sweetener, and (f) a buffering agent that maintains the pH of the solution within the range of about 2.5 to about 7. The solution does not comprise a barium-sulfate contrast agent. Oral administration of the solution distends the small bowel lumen, and the solution retains water in the small bowel lumen during the enterography examination sufficient to maintain a distention of the small bowel lumen to obtain visualization and differentiation of the small bowel lumen from adjacent structures by the computed tomography or magnetic resonance imaging.

The liquid vehicle formulations may be provided in ready-to-use aqueous form. Alternatively, the formulations may be provided in liquid concentrates or powders to which water may be added by the user to form the liquid vehicle formulation to be mixed with the oral contrast agent.

In use, a liquid vehicle formulation having desired properties can be mixed by a clinician with an oral contrast agent and is administered to a patient undergoing CT, MR, or radiographic examination. The liquid vehicle formulation is mixed with a specific quantity of the oral contrast agent to achieve the desired concentration of the contrast agent in the admixture consumed by the patient.

DESCRIPTION OF THE FIGURES

FIG. 4B demonstrates the oral contrast agent in the ileum (I) where the HU measures 143 (compare FIG. 3B to FIG. 2C and FIG. 1A).

DETAILED DESCRIPTION OF THE INVENTION

Figure 1:
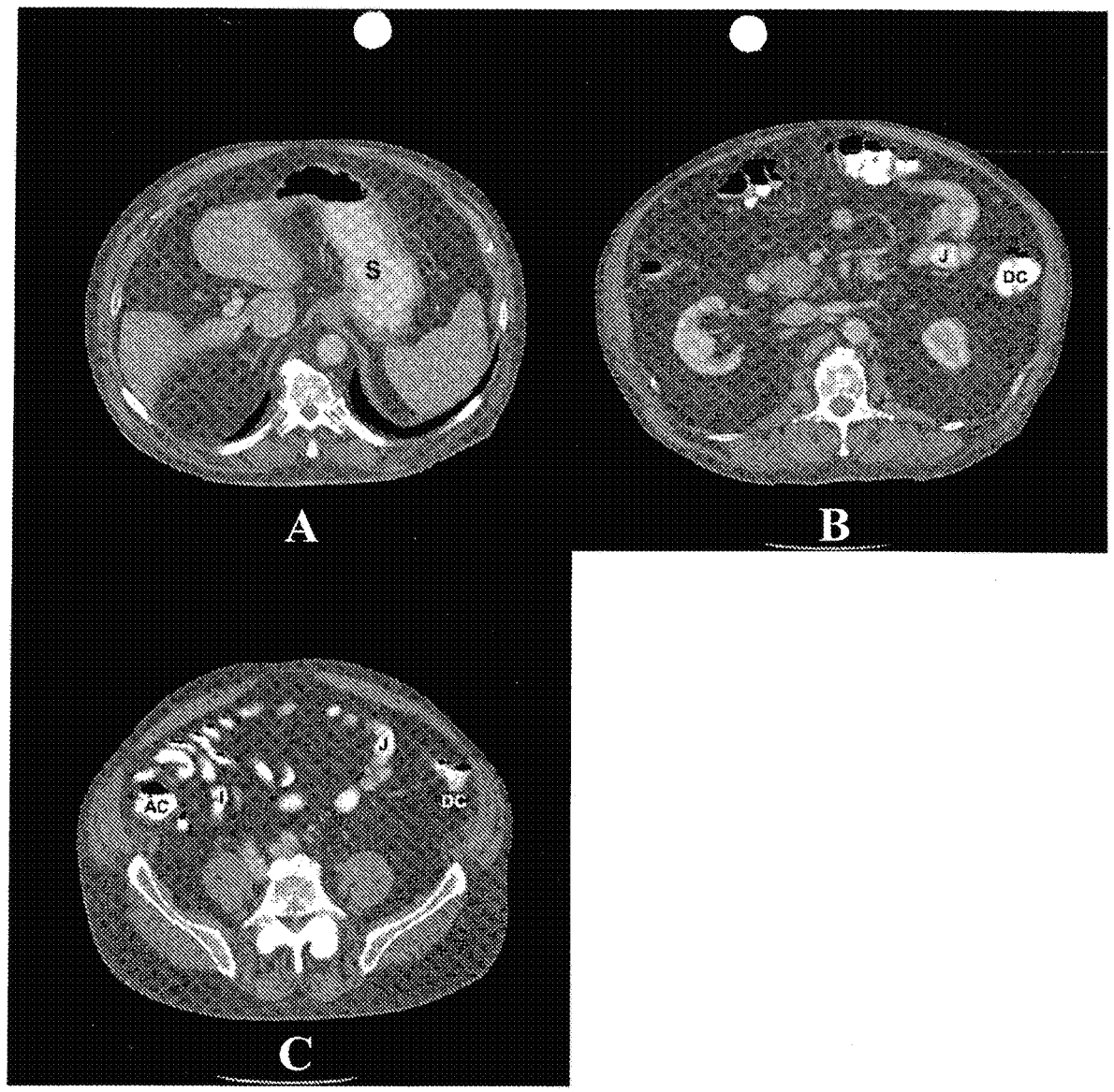
FIG. 1 shows CT images through the abdomen and pelvis of a patient to whom was administered a mixture of 30 mL of Gastrografin® oral contrast agent mixed with 970 mL of Tropical Punch Sugar Free Kool-Aid® beverage (Kraft Foods North America, Rye Brook, N.Y.). Image A demonstrates the admixed contrast material in the stomach (S), where the HU measures 179. Images B and C demonstrate the admixed contrast material in the jejunum (J) where the HU measures 258, in the ileum (I) where the HU measures 395, in the ascending colon (AC) where the HU measures 411, and in the descending colon (DC) where the HU measures 376.

The present invention relates generally to liquid vehicles that can be used by a physician, pharmacist, veterinarian, or other health professional to dilute or dissolve a pharmaceutical or non-pharmaceutical, water-soluble, oral contrast agent to provide a liquid formulation suitable for human or animal ingestion. The liquid vehicle may be provided in a ready-to-use aqueous solution. Alternatively, a powder or concentrated liquid may be provided that is dissolved or diluted in water by the end user to form the liquid vehicle to be used with the oral contrast agent. The liquid vehicles of the invention can serve as the basis for palatable and safe compounded oral contrast preparations.

The liquid vehicle formulations comprise an osmolality agent and may optionally further comprise one or more of viscosity agents, pH/buffering agents, palatability agents, preservatives, coloring agents, defoaming/surfactant agents and/or stability agents.

The terms "pharmaceutical oral contrast agent", "non-pharmaceutical oral contrast agent", "oral contrast agent", or "contrast agent" as used herein mean a product intended for use in the radiologic evaluation of a disease in a human or animal. More specifically, the terms mean a pharmaceutical or non-pharmaceutical water-soluble agent intended for oral ingestion that improves visualization or provides distension and demarcation of the gastrointestinal tract during radiologic imaging procedures, such as CT, MR, and conventional radiography.

A. Formulation

1. Osmolality Agents

The concentration of a dilute solution is usually expressed as its molality (moles per 1000 grams of solvent) or molarity (moles per 1000 mL of solution). In extremely dilute aqueous solutions, the molality and molarity can be assumed to be equal; with rising solute concentration the units deviate more and more to an extent dependent on the specific volume of the solute(s). For example, normal serum has a molality of 300 millimoles per 1000 grams of liquid, whereas the molarity is 282 millimoles per 1000 mL of serum. Osmolality and osmolarity indicate, respectively, the molality and molarity that an ideal solution of a non-dissociating substance must possess in order to exert the same osmotic pressure as the solution under consideration. For the concentrations and substances described in this application, osmolality and molality are considered as essentially interchangeable terms, and so are osmolarity and molarity.

As those skilled in the art will recognize, the osmolality of a solution may be controlled by regulating the use of osmotically active materials in the liquid vehicle formulation. Osmotically active materials include such physiologically compatible compounds as sugar alcohols, monosaccharide sugars, disaccharide sugars, oligosaccharides, polysaccharides, amino acids, and various synthetic compounds. Suitable monosaccharide sugars or sugar alcohols include, for example, erythrose, threose, ribose, arabinose, xylose, allose, altrose, glucose, mannose, idose, galactose, talose, ribulose, fructose, sorbitol, mannitol, and sedoheptulose. Suitable disaccharide sugars include, for example, lactose, sucrose, maltose, and cellobiose. Suitable amino acids include, for example, glycine, serine, threonine, cysteine, tyrosine, asparagine, glutamine, aspartic acid, glutamic acid, lysine, arginine and histidine. Synthetic compounds include, for example, propylene glycol, polypropylene glycol, ethylene glycol, polyethylene glycol, and polyvinylpyrrolidone. Various other suitable osmotically active materials are well known to those skilled in the art, and are intended to be within the scope of the term osmotically active agent as used herein.

All soluble material added to the liquid vehicle of the invention affects the measured osmolality. However, many solutes (like citric acid) are readily absorbed by the small bowel and after absorption no longer contribute to the actual osmolality of the liquid vehicle remaining within the bowel lumen. For this reason, the liquid vehicle of the invention contains one or more sugar alcohols as the osmotically active agent. Sugar alcohols include sorbitol, mannitol, erythritol, isomalt, maltitol, lactitol, and xylitol. Sorbitol and mannitol are sugar alcohols that are reported to be poorly absorbed by the gastrointestinal tract and thus retain their osmotic properties throughout bowel transit. In addition, sorbitol and mannitol are sugar alcohols that are well researched, readily available, and relatively inexpensive. However, any of the sugar alcohols can be substituted for sorbitol or mannitol in the liquid vehicle formulation.

Sorbitol is an alcohol derivative of glucose that has half the sweetening power of sucrose. It is commonly used as a sweetener and as a laxative. Sorbitol is absorbed by passive diffusion in the small intestine. The amount of sorbitol absorbed by the small intestine is variable, with a reported range from as little as 2% to as much as 100%. This large variation appears to be due to numerous experimental factors including: means of sorbitol administration, sorbitol concentration, sorbitol dose, fasting versus post-prandial state, subject adaptation to prior sorbitol exposure, presence of other solutes like glucose, individual patient differences, and the experimental method used for determination of absorption. Mannitol is an isomer of sorbitol with a similar sweetening power. Like sorbitol, mannitol can be absorbed by passive diffusion in the small intestine, with a reported absorption rate after oral administration ranging from 17% to 65%.

It is reported that the presence of a poorly absorbed sugar alcohol such as sorbitol or mannitol in the small bowel causes an isosmotic influx of both water and electrolytes into the bowel lumen. In fact, the measured small intestine fluid volume may be up to three times greater than that expected with an isosmotic solution of the unabsorbed sugar alone. In other words, the presence of unabsorbed sugar not only keeps water from being absorbed from the intestines; it also may lead to a net influx of other electrolytes into the bowel lumen that in turn results in water influx into the bowel lumen. This increase in bowel lumen fluid volume is believed to be a major cause of the accelerated small bowel transit time observed with sugar alcohol preparations. The degree of relative small bowel transit acceleration is proportional to the amount of unabsorbed sugar alcohol present in the small bowel lumen.

The two main benefits of these poorly-absorbed, osmotically-active sugars are faster transit through the bowel and retention of water in the GI tract. The latter keeps the liquid vehicle and any admixed oral contrast agents from becoming too concentrated during their transit through the gastrointestinal tract.

The liquid vehicles of the invention can be prepared with a variety of osmotically active materials that would provide a range of products from which the clinician could chose depending on the intended use. In some embodiments, the osmolality of the vehicle of the invention is 300 milliOsmoles (mOsmol) or less. In other embodiments, the osmolality is 250 mOsmol or less, or even 200 mOsmol or less. In some embodiments, the osmolality of a liquid vehicle of the invention is sufficiently low to allow the addition of a hypertonic oral contrast agent without the osmolality of the final preparation exceeding 300 mOsmol, which represents the osmolality of blood serum.

Sugar alcohols, including sorbitol, mannitol, erythritol, isomalt, maltitol, lactitol, and xylitol are typically used as the primary osmotic agent in the various formulations of the liquid vehicle, although the invention is not limited in this regard. In some embodiments, sorbitol and/or mannitol are used as the primary osmotic agent. Typically, to achieve the preferred ranges of osmolality in the liquid vehicle of the invention, less than about 200 grams/liter (20% w/v) of the osmotically active materials are employed. In some embodiments, less than about 100 g/L (10% w/v) of the osmotically active materials are employed, while in other embodiments, less than 40 g/L (4% w/v) of the osmotically active materials are employed. In particular embodiments, the range of osmotically-active ingredients is generally between about 0.01 and 40 g/L (0.001-4% w/v), depending on the particular osmotic agent used and the intended characteristics desired of a particular liquid vehicle. In some embodiments, the liquid vehicle relates to a formulation comprising between 0.001% to 4% w/v sorbitol and/or between 0.001% to 4% w/v mannitol.

Viscosity Agents

It has been reported that bowel transit is slowed when viscosity-increasing agents such as starch, gums, and cellulose are added to orally ingested solutions. It is also reported that the presence of viscosity agents, perhaps in part due to their effects on transit time, results in relatively increased bowel lumen distension compared to similar liquid vehicles that do not contain such viscosity agents. Therefore, in some embodiments of the liquid vehicle, the invention comprises a viscosity agent. Such agent may include any compound, including any fluid, semi-fluid or solid, that modifies the viscosity of a substance. Viscosity agents suitable for use herein may include, but are not limited to, artificial or natural hydrocolloid gums such as xanthan gum, carboxymethylcellulose, guar gum, locust bean gum, psillium gum, tamarind gum, tara gum, acacia, tragacanth gum, ghatti gums, methoxyl pectins, carrageenan, alginates, agarose, agar, fucellan, veegum, gum Arabic, microcrystalline cellulose, hydroxyethylcellulose, hydropropylcellulose, hydroxypropylmethylcellulose, gelatin, casein, and pectins.

Liquid vehicles of the invention can be prepared with a various quantities of viscosity agents to provide a range of products from which the clinician could choose depending upon the intended use. Vehicle embodiments containing greater quantities of viscosity agents are expected to provide slower bowel transit of admixed oral contrast agents and to provide increased bowel lumen distension compared with vehicle embodiments containing lesser quantities of equivalent viscosity agents.

Viscosity measurements are reported in centipoise (cP); one centipoise is equivalent to one milli-Pascal-seconds. Viscosity measurements of the liquid vehicles were performed at room temperature (23° C.), using a Brookfield dial reading LVT viscometer with a UL adapter 304 s/s and a spindle speed of 6 revolutions per minute (Brookfield Engineering Laboratories, Stoughton, Mass.).

In some embodiments of the liquid vehicle, the viscosity of the liquid vehicle is between 800 and 3000 cps when a slower transit time is desired with maximal bowel distension. In other embodiments, the viscosity of the liquid vehicle is between 200-800 cps when an intermediate transit time is desired with intermediate bowel distension. In yet other embodiments, the viscosity of the liquid vehicle is between 1-200 cps when a faster transit time is desired with less emphasis on the degree of bowel distension. These formulations require varied concentrations (w/v) of the viscosity agents in the liquid vehicle, depending on the particular viscosity agent utilized.

To achieve this range of measured viscosity, the liquid vehicle(s) are produced with a range of formulations. These formulations can include one or more of the hydrocolloid gums previously listed. In some embodiments, the liquid vehicle relates to a formulation comprising the hydrocolloid gums xanthan gum and/or carboxymethylcellulose. In some preferred embodiments, the liquid vehicle relates to a formulation comprising about 0.00001% to 5% w/v xanthan gum and/or about 0.00001% to 8% w/v carboxymethylcellulose.

2. pH/Buffering Agents

The liquid vehicle of the invention is buffered utilizing buffering agents that are Generally Regarded As Safe (GRAS) by the U.S. Food and Drug Administration. The pH of the liquid vehicle of the invention can be adjusted to the desired level by the addition of a weak acid to lower the pH. The addition of an appropriate quantity of a weak base to the liquid vehicle then buffers the vehicle and thereby helps to maintain the desired pH level, even when the liquid vehicle is subjected to an acidic environment such as in the stomach. Proper adjustment of the liquid vehicle pH and buffering capacity helps maintain solubility of admixed oral contrast agents and helps prevent precipitation or denaturation of the oral contrast agents.

Examples of suitable organic and inorganic acids include, but are not limited to, citric acid, malic acid, ascorbic acid, tartaric acid, lactic acid, acetic acid, phosphoric acid, maleic acid, fumaric acid, and adipic acid.

Examples of suitable bases include, but are not limited to: calcium carbonate, sodium carbonate, calcium bicarbonate, sodium bicarbonate, sodium hydroxide, potassium hydroxide, ammonium chloride, ammonium hydroxide, salts or basic salts of organic or inorganic acids, including citric acid, malic acid, ascorbic acid, tartaric acid, lactic acid, acetic acid, phosphoric acid, maleic acid, fumaric acid, and adipic acid.

The pH modifying and buffering agents included among the acids and bases listed above are well known to those skilled in the art and can be applied as needed.

The moderate tart or sour flavor provided by a liquid vehicle with pH from about 2.4 to about 4 has an antagonistic effect on bitter flavor notes, which are commonly introduced by the addition of oral contrast agents into the liquid vehicles of the invention. This antagonist effect is desirable to increase the overall palatability of the liquid vehicle/oral contrast admixture and serves as an additional reason for careful selection of the appropriate pH for the liquid vehicles.

Microbial growth is also suppressed at pH below 4 due to the bactericidal nature of the lower pH and the resulting higher relative quantity of protonated acid in the vehicle, allowing a reduction in the quantity of preservatives required to prevent spoilage in the required liquid vehicle.

Certain formulations of the liquid vehicle that are intended for use with ionic iodinated contrast agents have been specially formulated in regards to pH, ionic strength, buffering capacity, and chelating agents in order to minimize the chance of in vitro or in vivo precipitation of the contrast agent. This is further discussed below regarding the stability of the liquid vehicle.

Liquid vehicles of the invention may be prepared with a varying range of buffering agents, to provide a range of products with different pH values and buffering capacities, from which the clinician can chose dependent on the intended use. In some embodiments, the liquid vehicle relates to a formulation that comprises an organic acid. In some embodiments, the organic acid is citric acid and/or malic acid. In some embodiments, the liquid vehicle contains about 0.01% to 4% w/v citric acid and/or about 0.01% to 2% w/v malic acid.

In some embodiments, the liquid vehicle relates to a formulation that comprises the salt of an organic or inorganic acid as a buffering base. In some embodiments, the buffering base is the salt of citric acid, and/or phosphoric acid, and/or fumaric acid. In some embodiments, the salt of citric acid is sodium citrate and/or potassium citrate. In some preferred embodiments, the liquid vehicle formulation comprises about 0.001% to 3% w/v sodium citrate and/or 0.001% to 3% w/v potassium citrate.

In some embodiments, the acidic pH of the vehicle of the invention is produced by the addition of citric acid and/or malic acid, with buffering provided by the addition of the basic salt sodium citrate and/or potassium citrate, along with some buffering from the preservatives sodium benzoate, potassium benzoate, and sodium hexametaphosphate. The pH of the vehicle of the invention can be buffered to pH from about 2.5 to about 7.

3. Palatability Agents

A common formulation problem associated with liquid oral contrast agents is the presence of a disagreeable, often bitter, taste that is inherent in many of the oral contrast agents. Patients are often asked to consume large quantities of the diluted oral contrast agents prior to undergoing CT or MR imaging of the abdomen and pelvis (1000 mL for adults and 400-500 mL for children). It can prove difficult for some patients to consume these required quantities when the patient finds the formulation unpalatable. This is especially true for children and for patients with anorexia from their underlying medical condition (nausea, vomiting, chemotherapy, recent surgery, etc.). In view of these difficulties, it is desirable to develop a liquid vehicle formulation that is very palatable, using the correct ratio of sweeteners, flavors, and bitterness blockers to minimize the unpleasant taste of the oral contrast agents.

a. Sweeteners:

A liquid vehicle of the invention may include natural or artificial sweeteners. The sweetness of the vehicle is primarily produced by the use of artificial sweeteners.

Sweetening the vehicle of the invention primarily with an artificial sweetener makes the vehicle compatible with patients having blood glucose sensitivity. For example, patients with diabetes are sensitive to factors that change their blood glucose level. Even patients without diabetes can suffer adverse effects from sudden changes in their blood glucose levels. The blood glucose level is sensitive to the composition of substances taken orally. Diabetic patients undergoing CT and MR examination are usually fasting prior to their examinations and therefore have often decreased or eliminated their usual oral or injectable blood-glucose regulating medications. This makes the patient more prone to rapid swings in blood glucose levels if administered a large quantity of a liquid oral contrast formulation containing simple sugars. For these reasons it is prudent to formulate the liquid vehicle of the invention with artificial sweeteners for all potential users, diabetic or not.

Artificial sweeteners that may be used in the present invention include, but are not limited to, sucralose, acesulfame potassium, aspartame, saccharin, sodium saccharin, stevia, neotame, or mixtures thereof. The taste masking effective amount of an artificial sweetener is that amount whereby the taste of the bitter tasting contrast agent is masked, and the liquid vehicle/contrast agent composition is palatable.

Sweeteners have been used as stand-alone table-top products or have been mixed into food and beverage products, including vitamin and pharmaceutical vehicle preparations, to enhance flavor systems and to mask some unpleasant taste characteristics.

Sucralose is characterized as a trichlorinated carbohydrate, structurally similar to sucrose, having approximately 600 times the sweetening power of sucrose. Aspartame is characterized as a derivative of the dipeptide formed from the amino acids aspartic acid and phenylalanine, having approximately 180-200 times the sweetening power of sucrose. Acesulfame potassium is characterized as an oxathiazin salt, having approximately 200 times the sweetening power of sucrose. Acesulfame potassium has been proven to have a complementary sweetness profile to sucralose and aspartame, and is often used together with these sweeteners in relatively defined ratios to better imitate the sweetness profile of sucrose, which is considered the gold standard for optimal sweetness profile. Saccharin is characterized as a benzoic sulfinide, having approximately 500 times the sweetening power of sucrose. Saccharin sodium, which is considerably more soluble in water than saccharin, is used more frequently in pharmaceutical formulations and has approximately 300 times the sweetening power of sucrose. Stevia is characterized as a plant-derived sweetener. The primary stevia extract used for sweetening is rebaudioside A, having approximately 300 times the sweetening power of sucrose. Neotame is characterized as a derivative of the dipeptide formed from the amino acids aspartic acid and phenylalanine, having approximately 8000 times the sweetening power of sucrose.

As previously mentioned with regards to acesulfame potassium, mixtures of more than one sweetener have been found to have synergistic sweetening properties and improved taste characteristics compared with single sweetening agents used alone. The sweetness and/or taste of these artificial sweeteners can be modulated somewhat by the addition of small amounts of nutritive sweeteners. Such mixtures of nutritive and non-nutritive sweetening agents can be further modified by other ingredients, such as flavors and acids, to balance sweetness.

Optional nutritive sweetening agents include, but are not limited to, sugar sweeteners such as monosaccharides, disaccharides, oligosaccharides, and polysaccharides. Examples of suitable sugar sweeteners include but are not limited to sucrose, glucose, fructose, xylose, ribose, mannose, galactose, dextrose, maltose, partially hydrolyzed starch (such as maltitol syrup) or corn syrup solids, sugar alcohols such as sorbitol, mannitol, xylitol, glycerin, and combinations thereof. The amount of sugar sweetener used for taste masking will vary depending on the degree of palatability desired for the liquid vehicle composition and the taste profile of the oral contrast agent. Generally the total amount of nutritive sweetener used ranges from about 0.001% to 3% w/v.

In some embodiments, the liquid vehicle comprises a taste masking effective amount of a primary artificial sweetener and an optional secondary amount of a nutritive sweetener. Vehicles of the invention can be prepared with a varying range of nutritive and non-nutritive sweetening agents that would provide a range of products with different sweetness characteristics from which the clinician could chose dependent on the intended use.

In some embodiments, the taste masking effective amount of primary sweetener comes from an artificial sweetener. In some embodiments, the artificial sweetener comprises sucralose, acesulfame potassium, aspartame, saccharin, sodium saccharin, stevia, neotame, or mixtures thereof. In some embodiments the artificial sweetener is sucralose or acesulfame potassium. In some preferred embodiments, the liquid vehicle formulation contains about 0.0001% to 0.1% w/v sucralose and about 0.0001% to 0.1% w/v acesulfame potassium.

An optional secondary nutritive sweetener may be utilized to enhance the flavor and sweetness of the liquid vehicle. In some embodiments of the liquid vehicle, the secondary sweetener is a sugar alcohol, such as sorbitol, mannitol, erythritol, isomalt, maltitol, lactitol, and xylitol. In some embodiments, the secondary sweetener is sorbitol and/or mannitol. In some preferred embodiments the liquid vehicle formulation contains about 0.001% to 4% w/v sorbitol and about 0.001% to 4% w/v mannitol.

b. Flavors

Flavoring agents are important components of the composition and are included in amounts effective to provide a palatable flavor to the liquid vehicle/oral contrast mixture. The flavoring agent used is of the type and amount desired to enhance the palatability of the particular liquid vehicle/oral contrast mixture for the intended consumer.

Flavoring agents that may be used in the present invention include, but are not limited to, natural flavors, natural fruit flavors, artificial flavors, artificial fruit flavors, and flavor enhancers, or mixtures thereof. Natural flavors, artificial flavors or mixtures thereof include, but are not limited to, mint (such as peppermint or spearmint), menthol, cinnamon, vanilla, artificial vanilla, chocolate, artificial chocolate, coffee, toffee, butterscotch, nut (such as almond or walnut), tea, root beer, pina colada, or bubblegum. Natural fruit flavors, artificial fruit flavors or mixtures thereof include, but are not limited to, cherry, coconut, grape, orange, fruit punch, tropical punch, lime, peach, strawberry, banana, mango, pineapple, papaya, apple, blueberry, blackberry, boysenberry, watermelon, cantaloupe, apricot, grapefruit, guava, key lime, tangerine, black cherry, honeydew, pear, nectarine, plum, pomegranate, pumpkin, raspberry, and lemon. Flavor enhancers include, but are not limited to, acidulents like citric acid and malic acid, and salts like sodium citrate.

Liquid vehicles of the invention may be prepared with different flavoring agents that would provide a range of products with flavors from which the clinician could chose dependent on the intended use. Individual patients have different likes and dislikes when it comes to desired beverage flavors. By providing a variety of liquid vehicles, each with a different flavor, the clinician has the ability to mix the oral contrast agent with the patient's desired flavor of liquid vehicle, which may enhance patient compliance with consumption of the contrast agent. In some embodiments of the invention, a liquid flavoring agent used in the taste masking composition has a concentration ranging from about 0.015% to 0.5% v/v.

c. Bitterness Blockers

An optional debittering agent may be employed as a further part of the composition for taste masking. Optional debittering agents include, but are not limited to, natural debittering agents, artificial debittering agents, debittering agents which inhibit a chemosensory response in the mouth or nose, or mixtures thereof. Debittering formulations for use in the present invention are commercially available, including, but not limited to, those marketed under the names Prosweet® FL N&A (Virginia Dare, Brooklyn, N.Y.), Bitterness Modifier (International Flavors & Fragrances, New York, N.Y.), Masking Flavor MWNI (product numbers 109-18-A and 28-03-0162, E. A. Weber & Company, Wheeling, Ill.), and may be identified by those skilled in the art. In addition, single agent debittering agents may be utilized. Examples include nucleotides of the purine or pyrimidine group, or derivatives thereof, combined with an ionizable phosphate or other anionic organic compound.

Many times, flavors and flavor-masking ingredients are used to camouflage a variety of undesirable and unpleasant tastes caused by oral contrast agents, artificial sweeteners, and preservatives. Bitterness blockers are specially designed natural and/or artificial flavors that block the tongue's taste receptors' ability to taste bitterness and astringency, leading to fewer off-taste issues associated with functional ingredients, like oral contrast agents, preservatives, and artificial sweeteners. The bitterness blockers work synergistically when combined with other carefully selected flavor components, producing flavorings that are tailored to solve specific flavor problems in particular applications.

Bitterness blockers overcome undesirable taste components by selectively influencing the tongue's taste buds. To experience a taste sensation a molecule has to fit exactly onto a relevant receptor on the tongue. The debittering agent blocks the receptor by attaching itself to the receptor but does not itself trigger the taste sensation. That principle is similar to a "lock and key". In this case the taste receptor is acting as a lock. The fitting in of the key represents the molecule reception, while the opening of the lock is the taste sensation. The specialty of the bitterness blocker is that while it, like a "key", fits into the taste receptor "lock," it does not allow the opening of the lock, and thus prevents triggering of the taste experience. Therefore, undesirable and unpleasant tastes cannot be experienced.

Liquid vehicles of the invention may be prepared with different bitterness blocking agents, or without bitterness blocker if not needed, thus providing a range of products with different flavor characteristics from which the clinician can choose depending on the intended use. Different primary flavors (e.g., fruit punch versus lemon), different sweeteners (e.g., sucralose versus aspartame), different preservatives (e.g., potassium sorbate versus sodium hexametaphosphate), and different sourness profiles (e.g., citric acid versus fumaric acid) require different blocking agents and/or different quantities of blocking agent to maximize palatability. By providing a variety of liquid vehicles, each with a different optimized flavor profile, the clinician has the ability to mix the desired oral contrast agent with the patient's desired flavor of liquid vehicle, which may enhance patient compliance with full and timely consumption of the oral contrast agent. In some embodiments of the invention, a liquid bitterness blocking agent used as part of the taste masking composition has a range from about 0.001% to 1% w/v.

5. Other Functional Agents a. Preservatives

Preservatives useful in the present invention include, but are not limited to, sodium or potassium benzoate, sodium or potassium sorbate, salts of edetate (also known as salts of ethylenediaminetetraacetic acid, or EDTA, such as disodium edetate), parabens (such as methyl, ethyl, propyl and butyl p-hydroxybenzoic acids esters, or mixtures thereof), sodium or potassium hexametaphosphate, or mixtures thereof. The preservatives listed above are exemplary, but each preservative must be evaluated on an empirical basis, in each composition, to assure the compatibility and efficacy of the preservative. Methods for evaluating the efficacy of preservatives in liquid vehicle compositions are known to those skilled in the art. Sodium benzoate, potassium sorbate, sodium hexametaphosphate, and calcium disodium EDTA, or mixtures thereof, are the preferred preservative ingredients and may be added to the liquid vehicle of the invention although other acceptable preservatives may be substituted.

In some embodiments of the invention, the preservatives utilized are as follows: a preservative such as sodium benzoate may be optionally present in a range from about 0.001% to 0.2% w/v; a preservative such as potassium sorbate may be optionally present in a range from about 0.001% to 0.2% w/v; a preservative such as sodium hexametaphosphate may be optionally present in a range from about 0.001% to 0.3% w/v; and a preservative such as calcium disodium EDTA may be optionally present in a range from about 0.0001% to 0.005% w/v.

In some embodiments, the vehicle of the invention is sterile due to aseptic filling or hot fill manufacturing. In these embodiments, preservatives may or may not be included in the vehicle. In some embodiments, the vehicle of the invention is provided in a powdered form for liquid reconstitution and preservatives may or may not be included in the powdered form of the invention.

If preservatives are not utilized in the formulation, then the liquid vehicle is passed through a commercial high temperature short time pasteurization unit, where the product is heated to a sterilizing temperature for a few seconds and bottled into heat-tolerant PET bottles.

b. Coloring Agents

Coloring agents also may be incorporated to provide an appealing color to the liquid vehicle of the invention. Suitable coloring agents are well known to those skilled in the art and are those that avoid chemical incompatibilities with other ingredients.

Small amounts of one or more coloring agents may be utilized in the compositions of the present invention. FD&C dyes (e.g., yellow #5 and #6, blue #1 and #2, red #3 and #40, green #3) and/or FD&C lakes are preferably used. Additionally, a mixture of FD&C dyes or FD&C lake dyes in combination with other conventional food colorants may be used. Additionally, other natural coloring agents may be utilized including, for example, fruit, vegetable, and/or plant extracts such as those from grape, black currant, aronia, carrot, beetroot, red cabbage, and hibiscus.

Liquid vehicles of the invention can be prepared with different flavoring agents that would provide a range of products with flavors from which the clinician could chose dependent on the intended use. To correspond with the different flavoring agents, one or more coloring agents may be utilized to provide the beverage color usually associated with that flavor (e.g., purple color for grape flavor, yellow color for lemon flavor). By providing a variety of liquid vehicles, each with a different flavor and corresponding color, the clinician has the ability to mix the desired oral contrast agent with the patient's desired flavor of liquid vehicle, which may enhance patient compliance with full and timely consumption of the oral contrast agent.

The amount of coloring agent used will vary, depending on the agents used and the intensity desired in the finished product. The amount can be readily determined by one skilled in the art. In some embodiments of the invention, the powdered coloring agent has a range of about 0.01% to 1% w/v. In some embodiments, the liquid vehicle is colorless so as to avoid staining when spilled and to avoid confusion with other bodily fluids if spilled or regurgitated.

c. Defoaming/Surfactant Agent

Surfactant material can be helpful in blending the liquid vehicle, blending the liquid vehicle with the oral contrast agent, and increasing the compatibility of the liquid vehicle with the patient. Surfactant or surfactant-like molecules can also act as defoaming agents. Such agents include, but are not limited to, anionic surfactants, non-ionic surfactants, amphoteric surfactants, and others. Useful surfactants include, for example, sulfonate and sulfate surfactants, polyethylene glycols, polyethylene glycol esters, polyethylene glycol ethers, sorbitan materials known as Span® and Tween® materials, and polyalkylene oxide surfactants also known as pluronic or reverse pluronic surfactants. Siloxane polymers, such as simethicone, are useful for reducing foaming that is likely to occur when the vehicle is shaken or vigorously agitated. These materials are typically added at relatively low amounts and in some embodiments of the invention can be used at levels of about 0.0001% to 1% w/v.

B. Stability

It is impossible to anticipate every possible pharmaceutical or non-pharmaceutical oral contrast agent that may be compounded into a liquid vehicle of the invention. Some contrast agents can adversely affect the solubility properties of the preparation. The liquid vehicle of the invention is intended to provide a stable environment in which the admixed oral contrast agent remains solubilized. However, the solubility of oral contrast agents in any liquid vehicle can be affected by a variety of conditions, including, but not limited to, the pH of the compounded solution; the ionic strength of the compounded solution; the Lewis acidity/basicity of the added ingredients/solution; the physical conditions of the preparation, including temperature; the amount of time the combined product is stored; and the presence of metals and/or chelating agents.

Liquid vehicles of the invention preferably maintain their form and solubility function even after chemical or physical perturbation. A vehicle of the invention can tolerate a variety of perturbations including, but not limited to, changes in ionic strength, Lewis acidity/basicity of added ingredients, physical conditions of preparation and storage including refrigeration, and the presence of metals and/or chelating agents. Furthermore, liquid vehicles of the invention may be specifically formulated to maintain the solubility of specific oral contrast agents when exposed to gastrointestinal conditions, like body temperature and low pH conditions found in the stomach.

Figure 4:
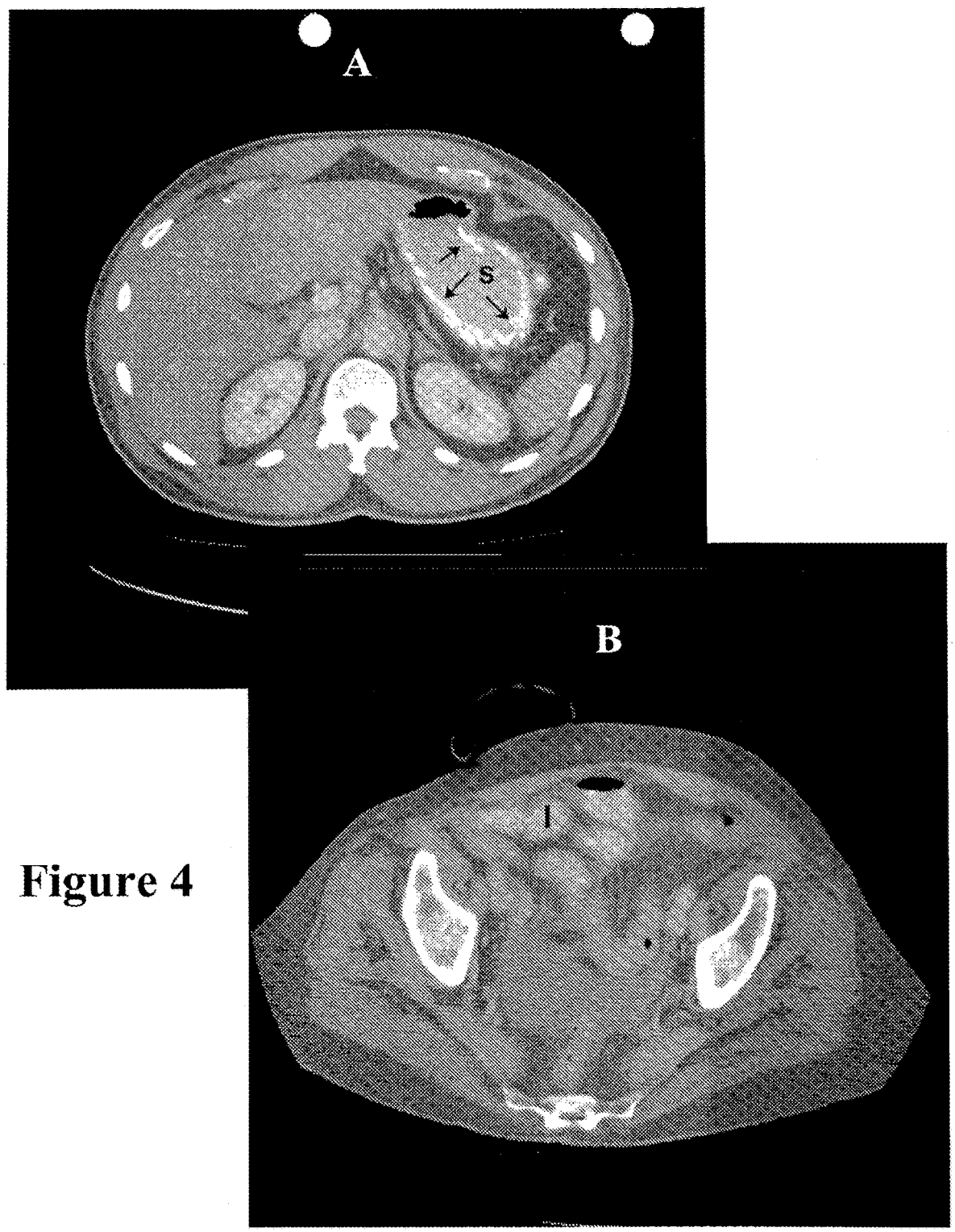
FIG. 4 shows an axial image through the abdomen of a patient to whom was administered a mixture of 30 mL of Gastrografin® oral contrast agent mixed with 970 mL of Kool-Aid® beverage. The black arrows in FIG. 4A point to the white precipitate (diatrizoic acid) that can sometimes form along the border of the stomach, due to precipitation of the Gastrografin's® diatrizoate salts in the acidic environment of the stomach. The precipitation of the contrast agent in the stomach lowers the HU of the remaining liquid oral contrast in the stomach (compare FIG. 4A to FIG. 2A and FIG. 1A). As a consequence, as the lower-HU oral contrast passes from the stomach into the remainder of the bowel the density of the contrast is less than would normally be expected.

Dilute aqueous solutions of ionic iodinated contrast media are among the most commonly used oral contrast agents for bowel opacification during computed tomography. Several scientific articles have described the precipitation of ionic iodinated contrast agents when exposed to low pH environments. The oral ionic contrast media currently utilized in the United States are the meglumine, sodium, or combination meglumine/sodium salts of the fully substituted tri-iodobenzoic acid derivative, diatrizoic acid. The salts of this moderately strong organic acid are freely soluble in water. The ionic contrast media dissociate in solution to form the radiopaque anion and a cation. The commercially available ionic oral contrast agents have pH ranging from 6.5 to 7.5. When these contrast agents are diluted with a low pH beverage, the contrast agent is exposed to an increased number of 'free' H$^+$ ions. The H$^+$ ions can combine with the diatrizoate anion to form diatrizoic acid. Diatrizoic acid is practically insoluble in water and precipitates out of solution forming white crystals (see FIG. 4). Data suggest that the rate of precipitation is dependent on pH, time, and temperature. As pH decreases, precipitation occurs at a faster rate. The rate of precipitation is slowed slightly by lower temperatures.

The result of experiments performed while formulating different versions of the liquid vehicle of the invention have clearly demonstrated that precipitation of ionic iodinated contrast agents is predominantly pH dependent. Other factors that were experimentally determined to increase precipitation include longer dwell time of oral contrast agent in the low pH environment and higher temperature of the admixed product.

Certain embodiments of the liquid vehicle described herein that are intended for use with ionic iodinated contrast agents are formulated in regard to pH, ionic strength, buffering capacity, and chelating agents, to minimize the chance of in vitro or in vivo precipitation of the contrast agent.

C. Uses

There is often a need to administer oral contrast agents in liquid form to patients prior to CT, MR, or radiographic imaging of the abdomen/pelvis. The oral contrast agent may exist as a water-soluble solid that requires a liquid vehicle for reconstitution into a form that can be readily consumed by the patient. More commonly, the oral contrast agent may exist as a water-based liquid, supplied in a concentration that is not suitable for direct consumption and therefore requires dilution in a liquid vehicle prior to patient consumption.

Many water-soluble liquid or solid contrast agents can be dissolved in the vehicle of the invention and administered to a patient. A patient may be a human or an animal. The following are exemplary, non-limiting, pharmaceutical contrast agents that can be admixed with the invention: iodine-based contrast agents like iohexol, iopamidol, ioversol, sodium diatrizoate, and meglumine diatrizoate; gadolinium-based contrast agents like gadopentetate dimeglumine, gadobenate demeglumine, gadodiamide, gadoteridol, gadoversetamide; manganese-based contrast agents like mangafodipir trisodium; and related compounds. This list is not exhaustive, but contains the most common agents currently in use.

In a typical preparation, a desired volume of a liquid contrast agent is measured, added to the liquid vehicle of the invention, and then shaken to mix the liquids. Such preparation, when it involves a pharmaceutical contrast agent, is considered a form of pharmaceutical compounding and is performed under the direction of a physician, pharmacist, veterinarian, or other qualified end-user. A vehicle of the invention can be combined with a variable amount of the contrast agent, dependent on the contrast agent used and the desired imaging characteristics of the final composition as determined by the compounding physician or pharmacist. As an example, a liquid contrast agent like iohexol could be mixed with the liquid vehicle of the invention in a ratio of 30 mL of iohexol to 970 mL of the liquid vehicle to yield approximately 1000 mL of final composition. This technique is flexible and provides many options to the compounding physician or pharmacist to customize the final formulation for each patient.

Over 20 different formulations of the liquid vehicle of the invention have been devised. Most have been devised for use with a particular subset of oral contrast agents for a particular imaging modality. However, several formulations have a more universal applicability. In clinical applications, the liquid vehicles have proven safe, effective, palatable, and well-tolerated diluents for the various oral contrast agents with which they have been admixed.

The vehicle of the invention relates to a product that eventually must become a water-based liquid in order to perform its function as a liquid vehicle for the creation of dilute solutions of pharmaceutical or non-pharmaceutical oral contrast agents. In its most convenient form, some embodiments of the invention relate to bottled, fully constituted liquid vehicles that are shelf stable and ready for use. In alternative embodiments, the invention relates to a variety of packaged forms that can be reconstituted with water, or water-based liquid, by the physician, pharmacist, veterinarian, or other end-user. One such embodiment relates to a miscible powder form of the invention, which could be supplied in single-dose packets/container and/or a multi-dose container. The end-user would add water to the miscible powder, either in a supplied container already housing the miscible powder or in a separate container, and would then reconstitute the final form of the liquid vehicle of the invention by agitation or stirring of the powder and water mixture. Another such embodiment relates to a concentrated liquid form of the invention, which could be supplied in single-dose packets/containers and/or a multi-dose container. The end-user would add water to the concentrated liquid, either in a supplied container already housing the concentrated liquid or in a separate container, and would then reconstitute the final form of the liquid vehicle of the invention by agitation or stirring of the concentrated liquid and water mixture.

VI. EXAMPLES

The present invention may be better understood with reference to the following examples. These examples are intended to be representative of specific embodiments of the invention and are not intended as limiting the scope of the invention.

Example 1

Modification of Contrast Concentration Observed During Passage Through the Bowel Via Adjustment of Liquid Vehicle Formulation

TABLE 1

| | Formulation 4 | Formulation 10 | Formulation 14 | Ingredient Function |
|---|---|---|---|---|
| Purified water USP | q.s. to 100% volume | q.s. to 100% volume | q.s. to 100% volume | Diluent |
| Sorbitol USP | 2.2% w/v | 0.8% w/v | 0.5% w/v | Osmotic agent |
| Mannitol USP | 0% w/v | 0.2% w/v | 0.1% w/v | Osmotic agent |
| Citric acid, FCC | 0.2% w/v | 0.21% w/v | 0.28% w/v | Flavoring agent, acidulent, pH buffer |
| Malic acid, FCC | 0% w/v | 0.03% w/v | 0% w/v | Flavoring agent, acidulent, pH buffer |
| Sodium citrate, FCC | 0% w/v | 0.1% w/v | 0.05% w/v | Flavoring agent, base, pH buffer |
| Natural & artificial flavors | 0.17% v/v | 0.17% v/v | 0.14% v/v | Flavoring agents |
| Natural & artificial colors | 0.004% w/v | 0.004% w/v | 0% w/v | Coloring agent |
| Sucralose, FCC | 0.015% w/v | 0.015% w/v | 0.01% w/v | Sweetener |
| Acesulfame potassium, FCC | 0.015% w/v | 0.015% w/v | 0.01% w/v | Sweetener |
| Xanthan gum, FCC | 0% w/v | 0.01% w/v | 0.005% w/v | Viscosity agent |
| Sodium benzoate, FCC | 0% w/v | 0.015% w/v | 0.15% w/v | Preservative, pH buffer |
| Potassium sorbate, FCC | 0% w/v | 0.01% w/v | 0.01% w/v | Preservative, pH buffer |
| Sodium hexameta-Phosphate, FCC | 0% w/v | 0.1% w/v | 0.075% w/v | Preservative, pH buffer |
| Calcium EDTA, FCC | 0% w/v | 0.003% w/v | 0.003% w/v | Preservative |

Figure 2:
FIG. 2 shows CT images through the abdomen and pelvis of a patient to whom was administered a mixture of 30 mL of Gastrografin® oral contrast agent mixed with 970 mL of one formulation of the liquid vehicle of the invention (Formulation 10). Image A demonstrates the admixed contrast material in the stomach (S), where the HU measures 188. Images B and C demonstrate the admixed contrast material in the jejunum (J) where the HU measures 168, in the ileum (I) where the HU measures 278, in the ascending colon (AC) where the HU measures 310, and in the descending colon (DC) where the HU measures 298. Image D shows a coronal image of the bowel segments, which better demonstrates the progressive increase in contrast agent HU that occurs from the stomach to the colon.

Commonly used water-soluble oral contrast agents for CT include iodine-containing products like Gastrografin® and Omnipaque®. Gastrografin® contains 660 mg of diatrizoate meglumine and 100 mg of diatrizoate sodium per mL of solution. Omnipaque® 300 contains 647 mg of iohexol per mL of solution. The diatrizoate salts and iohexol are very poorly absorbed from the gastrointestinal tract (less than 2% in normal patients) and are excreted in the stool. Water is absorbed from the diluted oral contrast agents during their passage through the gastrointestinal tract. As water is absorbed the remaining contrast agent becomes more concentrated. The concentration of the oral contrast agent can be quantitatively determined by measurement of the Hounsfield unit of the agent within the bowel lumen. Qualitatively, the concentration can be determined by observation of the degree of opacity (whiteness) of the oral contrast agent within the bowel lumen during CT examination. Greater contrast concentration correlates with greater whiteness (brightness) of the contrast agent. FIGS. 1-2 show characteristic CT images of subjects administered 30 mL of Gastrografin® diluted with either Kool-Aid® beverage or liquid vehicle Formulation 10, respectively. HU measurements at various bowel locations, as listed in the description of the figures, demonstrate progressive concentration of the oral contrast agent as it passes from the stomach to the colon. The maximum concentration is less (lower HU) for the admixture with Formulation 10 than for the Kool-Aid® admixture. Less contrast concentration is desirable for most imaging applications.

Various formulations of the liquid vehicle of the invention have been designed to affect to varying degrees the amount of water absorbed from the oral contrast/liquid vehicle admixture as it passes through the gastrointestinal tract. The effect of the various formulations is dependent on both the nature and the concentration of the contrast agent used. Experimental observation of various liquid vehicle formulations admixed with different contrast agents is required to determine the average effect expected with each different admixture. While significant individual differences between subjects administered the same contrast agent/liquid vehicle admixture are clinically observed, evaluation of large numbers of subjects demonstrates reproducible trends that can be used when choosing a particular liquid vehicle formulation for use with a specific oral contrast agent when a specific diagnostic result is desired.

Figure 3:
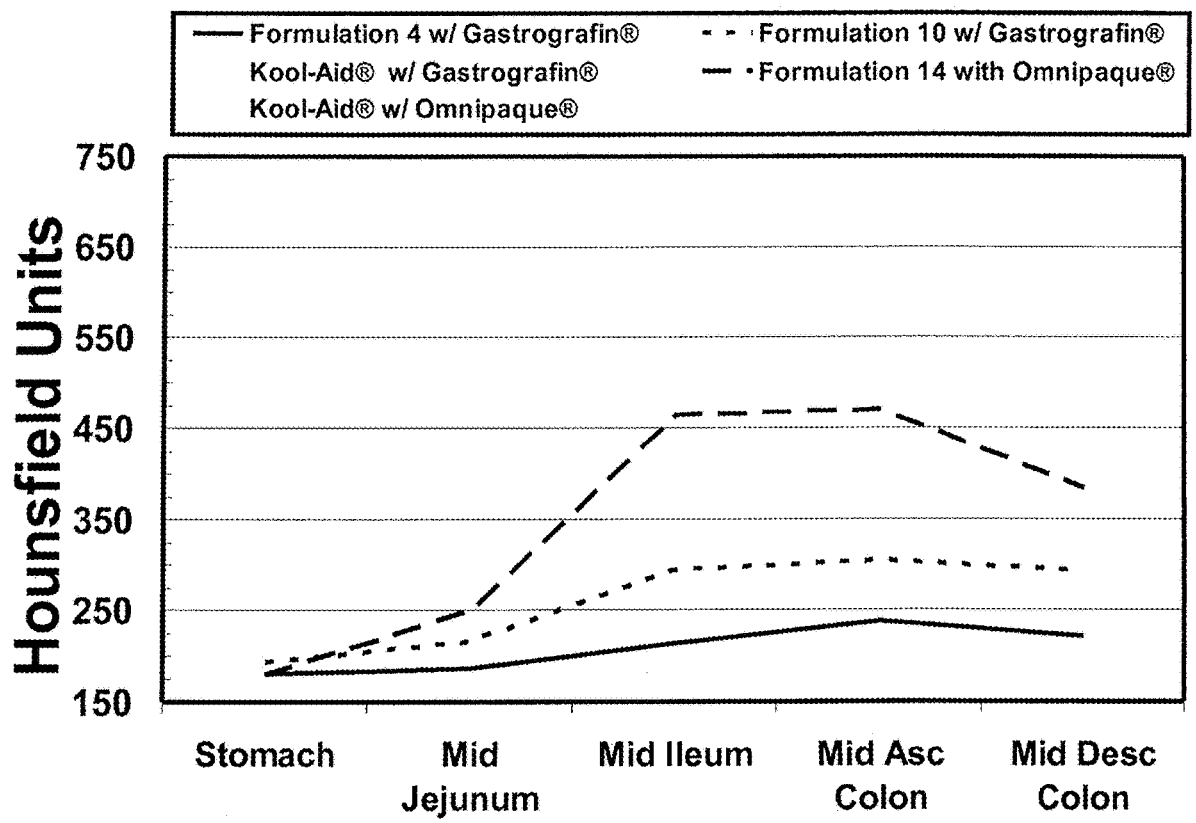
FIG. 3 demonstrates the average HU measurement in 5 separate portions of bowel as determined for different admixtures of contrast agent and liquid vehicle, including 3 different formulations of the liquid vehicle of the invention, as well as with Kool-Aid®. See Example 1 for a description of the various contrast agent/liquid vehicle formulations depicted in the graph.

FIG. 3 demonstrates the average HU measurement in five separate portions of bowel as determined for different admixtures of contrast agent and liquid dilution vehicle, including 3 different formulations of the liquid vehicle. For all measurements, the subjects were asked to fast overnight the day before contrast administration. The timing of oral contrast administration was as follows: 500 mL at 0 minutes, 250 mL at 30 minutes, 250 mL at 5 minutes before initiating the scan. The subjects were instructed to consume each allotment of contrast within 5 minutes. Contrast dilutions involving Gastrografin® were prepared by mixing 30 mL Gastrografin® with 970 mL of Kool-Aid® or with various formulations of the liquid vehicle. Contrast dilutions involving Omnipaque® were prepared by mixing 40 mL Omnipaque® 240 with 970 mL of Kool-Aid® or with various formulations of the liquid vehicle. A few of the various formulations that have been developed are included in this example for demonstration purposes. The liquid vehicle formulations were prepared in a manner similar to that described for the formulations listed in Example 2. Table 1 lists the ingredients found in Formulations 4, 10, and 14.

Example 2

Modification of Contrast Transit Time Through the Bowel Via Adjustment of Liquid Vehicle Formulation Several embodiments of the liquid vehicle of the invention contain the ingredients listed in Table 2:

TABLE 2

| | Formulation 4 | Formulation 10 | Formulation 18 | Ingredient Function |
|---|---|---|---|---|
| Purified water USP | q.s. to 100% volume | q.s. to 100% volume | q.s. to 100% volume | Diluent |
| Sorbitol USP | 2.2% w/v | 0.8% w/v | 0.4% w/v | Osmotic agent |
| Mannitol USP | 0% w/v | 0.2% w/v | 0.05% w/v | Osmotic agent |
| Citric acid, FCC | 0.2% w/v | 0.21% w/v | 0.25% w/v | Flavoring agent, acidulent, pH buffer |
| Malic acid, FCC | 0% w/v | 0.03% w/v | 0% w/v | Flavoring agent, acidulent, pH buffer |
| Sodium citrate, FCC | 0% w/v | 0.1% w/v | 0.07% w/v | Flavoring agent, base, pH buffer |
| Natural & artificial flavors | 0.17% v/v | 0.17% v/v | 0.16% v/v | Flavoring agents |
| Natural & artificial colors | 0.004% w/v | 0.004% w/v | 0% v/v | Coloring agent |
| Sucralose, FCC | 0.015% w/v | 0.015% w/v | 0.013% w/v | Sweetener |
| Acesulfame potassium, FCC | 0.015% w/v | 0.015% w/v | 0.01% w/v | Sweetener |
| Xanthan gum, FCC | 0% w/v | 0.01% w/v | 0.3% w/v | Viscosity agent |
| Carboxymethyl-cellulose, FCC | 0% w/v | 0% w/v | 0.3% w/v | Viscosity agent |
| Sodium benzoate, FCC | 0% w/v | 0.015% w/v | 0.01% w/v | Preservative, pH buffer |
| Potassium sorbate, FCC | 0% w/v | 0.01% w/v | 0.01% w/v | Preservative, pH buffer |
| Sodium hexametaphosphate. FCC | 0% w/v | 0.1% w/v | 0.05% w/v | Preservative, pH buffer |
| Calcium EDTA, FCC | 0% w/v | 0.003% w/v | 0.003% w/v | Preservative |

Formulations 4, 10, and 18 were prepared as follows:

A prehydrated, rapid dispersing xanthan gum in powdered form and carboxymethylcellulose in powdered form were added to heated purified water and agitated vigorously to form a thickener premix. Another premix was prepared by dispersing sodium hexametaphosphate in purified water preheated to 100° F. (37.8° C.). The xanthan gum/carboxymethylcellulose and sodium hexametaphosphate premixes were combined to provide a xanthan gum/carboxymethylcellulose/sodium hexametaphosphate mixture.

To this mixture were added sodium benzoate and potassium sorbate, followed by vigorous agitation. To this mixture were added calcium EDTA and the sweeteners, followed by vigorous agitation. The acidulents and buffering agents were prepared as a pre-mixed powder and added slowly to the aqueous mixture, followed by vigorous agitation until full dissolution occurred. The remaining ingredients (flavoring agents, coloring agents) were then added, followed by vigorous agitation. If preservatives were utilized in the formulation, the products were cold-filled under aseptic conditions into single-use PET bottles.

The primary differences between Formulations 4, 10, and 18, for purposes of this transit time evaluation, are in regards to the respective concentrations of the osmotic agents sorbitol and mannitol, and the viscosity agents xanthan gum and carboxymethylcellulose. Formulation 4, Formulation 10, Formulation 18, and Kool-Aid were mixed with equal quantities of oral iodinated contrast agents (30 mL of Gastrografin® per 970 mL of diluent) and administered to subjects prior to undergoing abdomen/pelvis CT imaging.

All subjects were asked to fast overnight. The timing of oral contrast administration was as follows: 500 mL at time equals 0 minutes, 250 mL at time equals 30 minutes, 250 mL at 5 minutes before initiating the scan. The subjects were instructed to consume each allotment of contrast within 5 minutes. The time between initiation of oral contrast administration (0 minutes) and scanning was recorded. The intended goal was to image each subject between one and two hours after initial contrast administration, although the actual time of imaging was dictated by the natural flow of the CT schedule.

Figure 6:
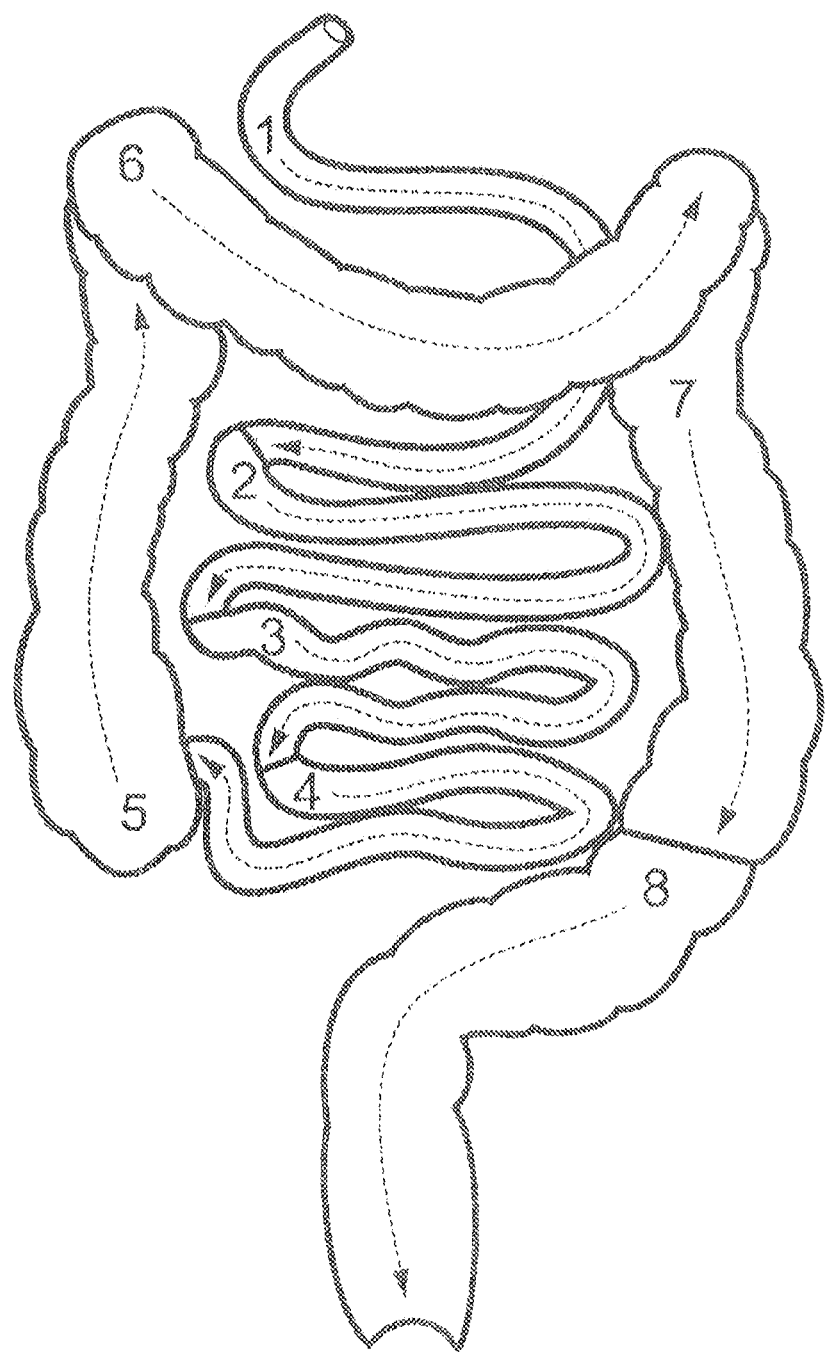
FIG. 6 shows a schematic drawing depicting a coronal view of the gastrointestinal tract. For purposes of transit time quantification the bowel was arbitrarily divided into the following 8 progression stages: 1=0-24% of small bowel, 2=25-49% of small bowel, 3=50-74% of small bowel, 4=75-99% of small bowel, 5=100% of small bowel to hepatic flexure, 6=hepatic flexure to splenic flexure, 7=splenic flexure to sigmoid colon, 8=sigmoid colon or rectum.

The distance traveled by the oral contrast was determined by recording the location of the most distal contrast within the bowel. For this purpose, the bowel was arbitrarily divided into the following 8 progression stages (FIG. 6): 1=0-24% of small bowel, 2=25-49% of small bowel, 3=50-74% of small bowel, 4=75-99% of small bowel, 5=100% of small bowel to hepatic flexure, 6=hepatic flexure to splenic flexure, 7=splenic flexure to sigmoid colon, 8=sigmoid colon or rectum. The stage was determined by one investigator who was blinded to product identity. Reproducibility of 96% for assigned progression stage (1-8) was found for our single blinded reader during a review of 50 consecutive patients. No consideration was given to the degree of opacification or distention of the bowel loops. No consideration was given to the presence or absence of intervening bowel loops without contrast. For data analysis, the distance traveled by a contrast agent in a given subject was standardized using that subject's time from initial oral contrast administration to scanning. This standardized stage number per unit time (as measured in hours) was calculated as [progression stage number divided by the time to scanning in hours]. For example Stage 8, achieved 2.0 hours after initial contrast administration, resulted in a standardized stage number per unit time of 'Stage 4 per hour' [8 divided by 2 equals 4]. This method of standardization was considered to be the best method for allowing comparisons of the distances traveled per unit time by the contrast agents. The standardization attempted to adjust for the fact that subjects were scanned at various times following initiation of contrast administration.

A review of the subjects' images revealed the following relative transit times (in units of standardized stage number per hour):
Gastrografin® with Kool-Aid: 3.7
Gastrografin® with Formulation 4: 4.5
Gastrografin® with Formulation 10: 4.2
Gastrografin® with Formulation 18: 3.8

Higher standardized stage number per unit time correlates with faster transit of the liquid vehicle/contrast agent through the gastrointestinal tract. This data demonstrates that oral contrast transit time can be influenced by the amount of osmotic agent and viscosity agent present in the liquid vehicle. This data, in conjunction with other data collected, provides quantitative information for the preparation of a range of liquid vehicles with varying transit times.

Figure 5:
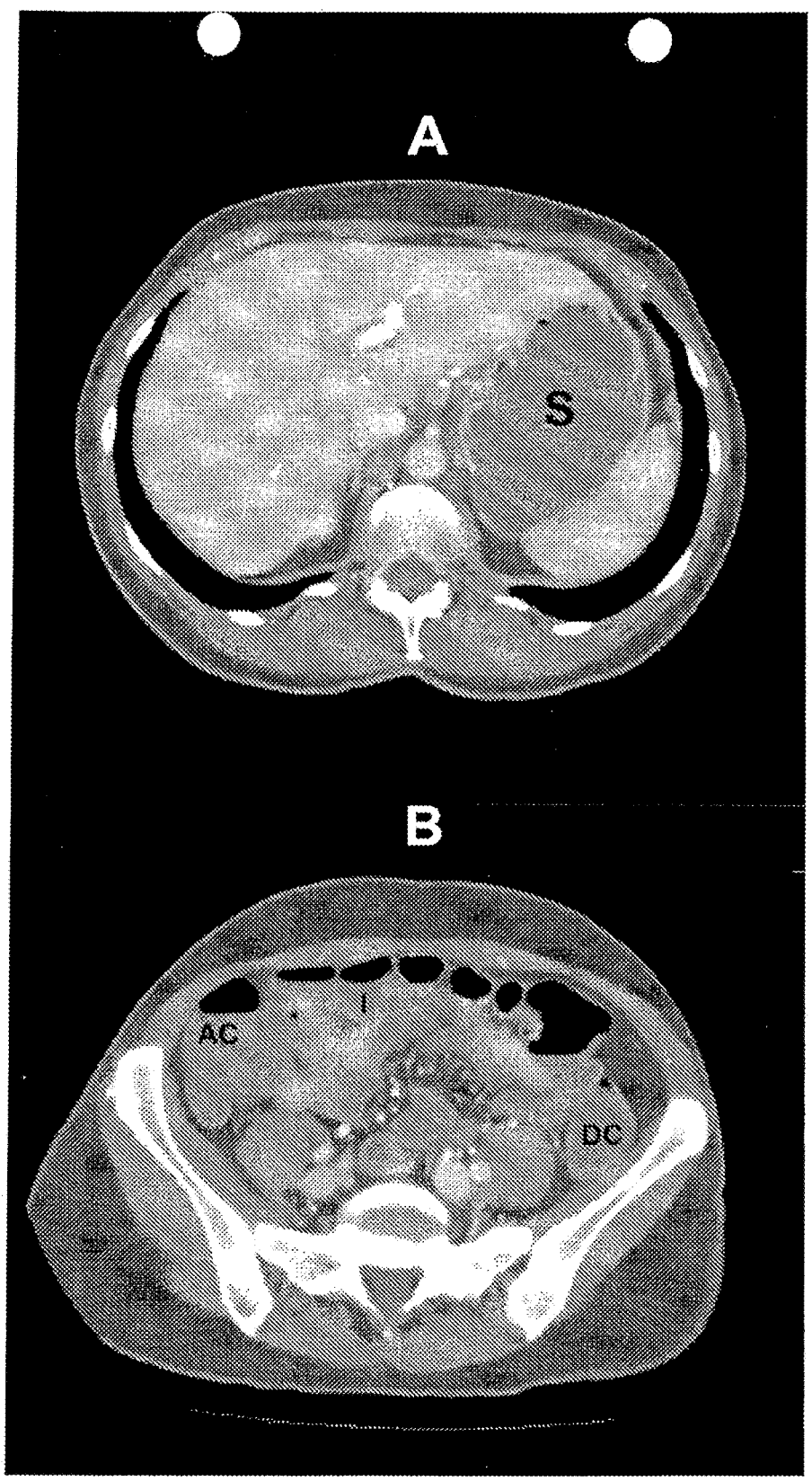
FIG. 5 shows axial images through the abdomen and pelvis of a patient to whom was administered a mixture of 1 mL of Omnipaque® (GE Healthcare, Princeton, N.J.) oral contrast agent mixed with 999 mL of liquid vehicle Formulation 18 (see Example 2). In this particular patient a very low concentration of oral contrast agent was used to allow improved visualization of the bowel wall. Image A demonstrates the admixed contrast material in the stomach (S), where the HU measures 10. Image B demonstrates the admixed contrast material in the ileum (I) where the HU measures 19, in the ascending colon (AC) where the HU measures 22, and in the descending colon (DC) where the HU measures 26. This formulation of the liquid vehicle is intended for use when the physician desires the oral contrast agent to move slowly through the gastrointestinal tract with increased bowel distension at each level.

FIG. 5 shows axial images through the abdomen and pelvis of a patient to whom was administered a mixture of 1 mL of Omnipaque® oral contrast agent mixed with 999 mL of Formulation 18 of the liquid vehicle of the invention. For this particular patient a very low concentration of oral contrast agent was used to allow improved visualization of the bowel wall. This formulation of the liquid vehicle is intended for use when the physician desires the oral contrast agent to move slowly through the gastrointestinal tract with maximum bowel distension at each level.

Example 3

Modification of Contrast Precipitation Rates Via Adjustment of Liquid Vehicle Formulation Several embodiments of the liquid vehicle of the invention contain the following ingredients:

TABLE 3

| | Formulation 4 | Formulation 10 | Formulation 20 | Ingredient Function |
|---|---|---|---|---|
| Purified water USP | q.s. to 100% volume | q.s. to 100% volume | q.s. to 100% volume | Diluent |
| Sorbitol USP | 2.2% w/v | 0.8% w/v | 0.5% w/v | Osmotic agent |
| Mannitol USP | 0% w/v | 0.2% w/v | 0.1% w/v | Osmotic agent |
| Citric acid, FCC | 0.2% w/v | 0.21% w/v | 0.17% w/v | Flavoring agent, acidulent, pH buffer |
| Malic acid, FCC | 0% w/v | 0.03% w/v | 0.01% w/v | Flavoring agent, acidulent, pH buffer |
| Sodium citrate, FCC | 0% w/v | 0.1% w/v | 0.15% w/v | Flavoring agent, base, pH buffer |
| Natural & artificial flavors | 0.17% v/v | 0.17% v/v | 0.14% v/v | Flavoring agents |
| Natural & artificial colors | 0.004% w/v | 0.004% w/v | 0% w/v | Coloring agent |
| Sucralose, FCC | 0.015% w/v | 0.015% w/v | 0.01% w/v | Sweetener |
| Acesulfame potassium, FCC | 0.015% w/v | 0.015% w/v | 0.01% w/v | Sweetener |
| Xanthan gum, FCC | 0% w/v | 0.01% w/v | 0.005% w/v | Viscosity agent |
| Sodium benzoate, FCC | 0% w/v | 0.015% w/v | 0.15% w/v | Preservative, pH buffer |
| Potassium sorbate, FCC | 0% w/v | 0.01% w/v | 0.15% w/v | Preservative, pH buffer |
| Sodium hexametaphosphate, FCC | 0% w/v | 0.1% w/v | 0.1% w/v | Preservative, pH buffer |
| Calcium EDTA, FCC | 0% w/v | 0.003% w/v | 0.003% w/v | Preservative |

The liquid vehicle formulations were prepared in a manner similar to that described for the formulations listed in Example 2.

The primary differences between Formulation 4, Formulation 10, and Formulation 20, for purposes of this precipitation evaluation, are in regards to the respective concentrations of the buffering agents citric acid, malic acid, sodium citrate, sodium benzoate, sodium hexametaphosphate, and potassium sorbate. Formulations 4, Formulation 10, Formulation 20, and Kool-Aid® were mixed with equal quantities of oral iodinated contrast agents (30 mL of Gastrografin® per 970 mL of diluent) and then administered to subjects prior to CT examination.

A review of the subjects' images revealed the following rates of oral contrast agent precipitation in the stomach:
Gastrografin® with Kool-Aid: 18%
Gastrografin® with Formulation 4: 15%
Gastrografin® with Formulation 10: 7%
Gastrografin® with Formulation 18: 2%

This data demonstrates that the propensity for precipitation of the oral contrast agents when exposed to gastric acid can be reduced by adjustment of the buffering capacity of the liquid vehicle. This data, in conjunction with other data collected, provides quantitative information for the preparation of a range of liquid vehicles with varying buffering capacity.

Example 4

Modification of Contrast Palatability Rates Via Adjustment of Liquid Vehicle Formulation Palatability is one factor physicians consider when choosing an oral contrast agent for CT because of its relevance to patients' compliance and comfort. A common formulation problem associated with liquid oral contrast agents is the presence of a disagreeable, often bitter, taste that is inherent in many of the oral contrast agents. Patients are often asked to consume large quantities of the diluted oral contrast agents prior to undergoing CT or MR imaging of the abdomen and pelvis (1000 mL for adults and 400-500 mL for children). It can prove difficult for some patients to consume these required quantities when the patient finds the formulation unpalatable.

Various oral contrast/liquid vehicle formulations were designed for improved palatability. Subjects ingested 1000 mL of these admixtures prior to CT examination. After the examination the subjects were given a paper questionnaire that they returned by mail. Part of the questionnaire was devoted to the palatability of the consumed product. Subjects were asked, "On a scale of 0 to 10, with 0 as very bad, and 10 as very good, how well did you like the taste of the product you drank? Please place an "X" on the line between 0 and 10." Responses were placed on the paper questionnaire using a visual analog rating scale from 0 to 10.

While many formulations were tested, a representative subset of the results is presented for the purposes of this Example. Formulation 4, Formulation 10, Formulation 14, and Kool-Aid were mixed with equal quantities of an oral iodinated contrast agent (30 mL of Gastrografin® per 970 mL of diluent) and administered to subjects prior to undergoing abdomen/pelvis CT imaging.

A review of the subjects' responses to the palatability questionnaire revealed the following average palatability scores:
Gastrografin® with Kool-Aid: 7.3
Gastrografin® with Formulation 4: 8.0
Gastrografin® with Formulation 10: 8.2
Gastrografin® with Formulation 14: 8.5

The primary differences between Formulations 4, 10, and 14, for purposes of this palatability evaluation, are in regards to the respective concentrations of: the sweetening agents sucralose, acesulfame potassium, sorbitol, and mannitol; the preservatives potassium sorbate, sodium benzoate, and sodium hexametaphosphate; the viscosity agent xanthan gum; the buffering agents citric acid, malic acid, and sodium citrate that affect sour/tangy taste sensations; and the choice and concentration of the natural and artificial flavorings, including bitterness blockers. This data demonstrates that oral contrast palatability can be significantly improved by the careful and appropriate formulation of all ingredients that affect palatability, especially when these ingredients are chosen to complement the inherent taste/bitterness of a particular oral contrast agent. These data, in conjunction with other data collected, provide quantitative information for the preparation of a range of liquid vehicles that best complement different oral contrast agents.

Example 5—Formulation for Ionic Contrast Agents

The following describes one embodiment of the oral vehicle for use with ionic iodinated contrast agents:
Formulation Per 1 Liter:
Sodium Hexametaphosphate (Glass H) 1 gm
Sodium Benzoate 0.15 gm
Potassium Sorbate 0.1 gm
Calcium Disodium EDTA 0.033 gm
Sucralose 0.145 gm
Acesulfame Potassium 0.11 gm
Sorbitol 2.5 gm=0.25%
Mannitol 0.5 gm=0.05%
Citric Acid 2.13 gm
Sodium Citrate 0.90 gm
Malic Acid 0.32 gm
Liquid Flavor 1.4 ml
Liquid Flavor 0.125 ml
   Add water to achieve 1 Liter total volume Example 6—Formulation for Non-Ionic Contrast Agents The following describes one embodiment of the oral vehicle for use with non-ionic iodinated contrast agents:
Formulation Per 1 Liter:
Sodium Hexametaphosphate (Glass H) 1 gm
Sodium Benzoate 0.15 gm
Potassium Sorbate 0.1 gm
Calcium Disodium EDTA 0.033 gm
Sucralose 0.1 gm
Acesulfame Potassium 0.04 gm
Sorbitol 7.5 gm=0.75%
Mannitol 1.5 gm=0.15%
Citric Acid 1.4 gm
Sodium Citrate 0.26 gm
Malic Acid 0.09 gm
Bell Liquid Flavor 0.95 ml
Xanthan gum 0.70 g/L=0.075%
Add water to achieve 1 Liter total volume Example 7—Neutral Formulation The following describes one embodiment of the oral vehicle for preparation of neutral density oral iodinated contrast agents.
Formulation Per 1 Liter:
Sodium Hexametaphosphate (Glass H) 1 gm
Sodium Benzoate 0.15 gm
Potassium Sorbate 0.1 gm
Calcium Disodium EDTA 0.033 gm
Sucralose 0.1 gm
Acesulfame Potassium 0.04 gm
Sorbitol 18 gm=1.8%
Mannitol 4 gm=0.4%
Citric Acid 1.4 gm
Sodium Citrate 0.26 gm
Malic Acid 0.09 gm
Liquid Flavor 0.95 ml
Xanthan gum 0.70 g/L=0.07%
Add water to achieve 1 Liter total volume
Formulation and Protocol for Oral Contrast Administration for Abdominal/Pelvic CT The following administration protocols and formulations may be used in embodiments of the invention for patients requiring oral contrast administration prior to undergoing abdominal/pelvic CT examination. It has been found that using the formulations of liquid dilution vehicles and contrast agents described below, and administering the contrast agent mixtures as described below, unexpectedly provided improved imaging using CT scans.

In one embodiment, the liquid dilution vehicle is mixed with a nonionic iodinated contrast agent. A quantity of a first formulation of the liquid dilution vehicle is mixed with a first quantity of nonionic iodinated contrast agent to form a first contrast agent mixture, and a quantity of a second formulation of the liquid dilution vehicle is mixed with a second quantity of nonionic iodinated contrast agent to form a second contrast agent mixture. One skilled in the art will recognize that the volumes of the first and second liquid dilution vehicles and the nonionic iodinated contrast agent may be varied as desired for administration to the patient. Any appropriate nonionic iodinated contrast agent known to those skilled in the art may be used. In one embodiment, Omnipaque™ (iohexol) is used as the nonionic iodinated contrast agent.

The liquid dilution vehicle and the nonionic iodinated contrast agent may be mixed in any appropriate type of container, such as for example a plastic bottle. The quantities of the first and second liquid dilution vehicle formulations used and the quantities of the nonionic iodinated contrast agents used are selected to achieve a desired concentration of the contrast agent when administered to a patient. In one embodiment, the first quantity of liquid dilution vehicle is mixed with the first quantity of nonionic iodinated contrast agent to achieve a total volume of about 500 mL and the second quantity of liquid dilution vehicle is mixed with the second quantity of nonionic iodinated contrast agent to achieve a total volume of about 500 ml. In this embodiment, the volumes may typically vary within tolerances of ± about 20 ml.

In one embodiment, a quantity of about 500 ml of a first contrast agent mixture is prepared by mixing about 483 ml of the first formulation of the liquid dilution vehicle described in Table 1 below with about 17 ml of Omnipaque 240, which contains 240 mg iodine/ml. The first liquid dilution vehicle and the Omnipaque may be mixed in a first plastic bottle. Alternatively, about 14 ml of Omnipaque 300 (300 mg iodine/nil) may be mixed with about 486 ml of the first liquid dilution vehicle, or about 12 ml of Omnipaque 350 (350 mg iodine/ml) may be mixed with 488 ml of the first liquid dilution vehicle.

In one embodiment, a quantity of about 500 ml of a second contrast agent mixture is prepared by mixing about 472 ml of the second formulation for the liquid dilution vehicle, described in Table 2 below, with about 28 ml of Omnipaque 240. The second liquid dilution vehicle and the Omnipaque may be mixed in a second plastic bottle. Alternatively, about 22 ml of Omnipaque 300 (300 mg iodine/ml) may be mixed with about 478 ml of the second liquid dilution vehicle, or about 19 ml of Omnipaque 350 (350 mg iodine/ml) may be mixed with 481 ml of the second liquid dilution vehicle.

The first and second bottles of contrast agent mixtures prepared as described above are sequentially administered to the patient prior to CT scanning. The time for consumption of each bottle prior to the CT scanning procedure may be adjusted to achieve the desired results. Typically, the patient should not eat any food or drink any fluid for at least 4 hours prior to ingestion of the oral contrast mixtures. In one embodiment, the patient consumes about half (i.e. 250 ml) of the first oral contrast agent mixture in the first bottle over a period of about 10 minutes. The remaining half of the first contrast agent mixture in the first bottle and then the entire quantity of the second contrast agent mixture in the second bottle are consumed evenly over about 50-60 minutes. Consumption of all of the oral contrast mixture is therefore complete in about 60-70 minutes after the start of consumption. CT scanning can be performed about 70-75 minutes after the start of consumption.

For most patients, the protocol described above provides relatively uniform enhancement of the stomach and small bowel. The degree of colonic enhancement can vary between patients. If gastric opacification is of particular concern, then the protocol can be adjusted by administering a greater proportion of the oral contrast mixture at the end of the administration period or an additional quantity of the second oral contrast mixture can be prepared and administered shortly before the CT scan.

The following Table provides the ingredients to be included in the first liquid dilution vehicle in the embodiments described above.

TABLE 1

Formula for First Liquid Dilution Vehicle Formulation per 1 Liter:

Xanthan Gum - about 0.30 to 1.20 g, preferably about 0.75 g
Sodium Hexametaphosphate - about 0.5 to 1.5 g, preferably about 1 g
Sodium Benzoate - about 0.05 to 0.25 g, preferably about 0.15 g
Potassium Sorbate - about 0.05 to 0.15 g, preferably about 0.1 g
Calcium Disodium EDTA - about 0.01 to 0.04 g, preferably about 0.033 g
Sucralose - about 0.05 to 0.15 g, preferably about 0.1025 g
Acesulfame Potassium about 0.020 to 0.070 g, preferably about 0.0476 g
Sorbitol - about 9.5 to 19.5 g, preferably about 14.375 g
Mannitol - about 1.00 g to 5.00 g, preferably about 2.875 g
Citric Acid - about 1.0 to 2.0 g, preferably about 1.52 g
Sodium Citrate - about 0.05 to 0.30 g, preferably about 0.16 g
Malic Acid - about 0.05 to 0.15 g, preferably 0.09 g
Liquid Flavor, for example lemon flavor or lemon-lime flavor - about 0.70 to 1.5 ml, preferably about 0.93 mL
Add water to achieve about 1 Liter total volume (approximately 985 ml water plus dry ingredients = 1 Liter).

The following Table provides the ingredients to be included in the second liquid dilution vehicle in the embodiments described above.

TABLE 2

Formula for Second Liquid Dilution
Vehicle Formulation per 1 Liter:

Xanthan Gum - about 0.30 to 1.20 g, preferably about 0.75 g
Sodium Hexametaphosphate - about 0.5 to 1.5 g, preferably about 1 g
Sodium Benzoate - about 0.05 to 0.25 g, preferably about 0.15 g
Potassium Sorbate - about 0.05 to 0.15 g, preferably about 0.1 g
Calcium Disodium EDTA - about 0.01 to 0.04 g, preferably about 0.033 g
Sucralose - about 0.05 to 0.15 g, preferably about 0.11 g
Acesulfame Potassium - about 0.02 to 0.07 g, preferably about 0.05042 g
Sorbitol - about 2.0 to 9.0 g, preferably about 4 g
Mannitol - about 0.5 to 5.0 g, preferably about 0.8 g
Citric Acid - about 1.0 to 2.0 g, preferably about 1.52 g
Sodium Citrate - about 0.05 to 0.30 g, preferably about 0.16 g
Malic Acid - about 0.05 to 0.15 g, preferably 0.09 g
Liquid Flavor, for example lemon flavor or lemon-lime flavor - about 0.70 to 1.5 ml, preferably about 1.02 mL
Add water to achieve about 1 Liter total volume (approximately 985 ml water plus dry ingredients = 1 liter).

Formulation and Protocol for Dedicated Small Bowel CT, Abdominal/Pelvic CT, or PET/CT The following formulations and administration protocols may be used in embodiments of the invention for patients requiring administration of a neutral Hounsfield unit (HU) intraluminal oral agent prior to undergoing small bowel CT examination, abdominal/pelvic CT or PET/CT. It has been found that using the formulations of neutral HU liquid vehicles described below, and administering the neutral HU liquid vehicles as described below, unexpectedly provided improved imaging using CT scans, particularly for dedicated imaging of the small bowel or other gastrointestinal segments where a neutral HU intraluminal oral agent (hereafter referred to as a "neutral liquid vehicle") is desired to provide bowel identification and distension.

In one embodiment that may be used for dedicated CT small bowel imaging, the neutral liquid vehicle having the formulation described in Table 3 may be administered over a period of about 60 minutes as follows. A first bottle of the neutral liquid vehicle is steadily consumed (by sipping) over a period of up to about 20 minutes. After the first bottle is entirely consumed, a second bottle of the neutral liquid vehicle is steadily consumed (by sipping) over a second period of up to about 20 minutes. After the second bottle is entirely consumed, the patient will then steadily consume (by sipping) either (1) a third bottle of the neutral liquid vehicle or (2) about 500 ml of water over a third period of up to about 20 minutes. CT scanning of the patient may be performed about 60-70 minutes after the patient takes the first sip of the neutral liquid vehicle. In one embodiment, each bottle of neutral liquid vehicle contains about 500 ml± about 20 ml.

In another embodiment that may be used for abdominal/pelvic CT imaging the neutral liquid vehicle having the formulation described in Table 3 may be administered over a period of about 60 minutes as follows. The patient consumes about half (e.g. about 250 ml) of the neutral liquid vehicle in a first bottle over a period of about ten minutes. The remaining half of the first bottle (e.g. about 250 ml) and then the entire quantity of the neutral liquid vehicle in a second bottle (e.g. about 500 ml) are consumed evenly over about 50-60 minutes. Consumption of all of the neutral liquid vehicle is therefore completed within about 60-70 minutes after the start of consumption. CT scanning of the patient can be performed about 70-75 minutes after the start of consumption.

In another embodiment of the invention, an ionic or nonionic iodinated contrast agent may be mixed with the liquid dilution vehicle having the formulation described in Table 3 to produce a near-neutral HU contrast agent mixture. Approximately 1-3 ml of the ionic or nonionic contrast agent is mixed with the liquid dilution vehicle to produce approximately 500 mL of the near-neutral HU contrast agent mixture. This contrast agent mixture may be useful in applications where a minimal amount of positive Hounsfield unit density is desired. The contrast agent mixture may be administered using one of the administration protocols described in the paragraphs above.

The iodinated contrast agent and the liquid dilution vehicle are mixed in any appropriate container, such as for example a plastic bottle. Depending on the administration protocol that will be used, it may be necessary to prepare and administer more than one bottle of the contrast agent mixture. Each bottle typically contains about 1 ml of the ionic or nonionic contrast agent diluted by the liquid dilution vehicle described in Table 3 to obtain about 500 ml±20 ml of the contrast agent mixture.

The following Table provides the ingredients to be included in the neutral liquid vehicle/liquid dilution vehicle described in the above embodiments.

TABLE 3

Formula for Small Bowel Neutral Liquid Vehicle/Liquid Dilution Vehicle Formulation per 1 Liter:

Xanthan Gum - about 0.30 to 1.20 g, preferably about 0.75 g
Sodium Hexametaphosphate - about 0.5 to 1.5 g, preferably about 1 g
Sodium Benzoate - about 0.05 to 0.25 g, preferably about 0.15 g
Potassium Sorbate - about 0.05 to 0.15 g, preferably about 0.1 g
Calcium Disodium EDTA - about 0.01 to 0.04 g, preferably about 0.033 g
Sucralose - about 0.05 to 1.5 g, preferably about 0.09809 g
Acesulfame Potassium - about 0.02 to 0.07 g, preferably about 0.04553 g
Sorbitol - about 12.0 to 19.9 g, preferably about 16.5 g
Mannitol - about 1.5 to 7.0 g, preferably about 3.3 g
Citric Acid - about 1.0 to 2.0 g, preferably about 1.52 g
Sodium Citrate - about 0.05 to 0.30 g, preferably about 0.16 g
Malic Acid - about 0.05 to 0.15 g, preferably about 0.09 g
Liquid Flavor, for example lemon flavor or lemon-lime flavor - about 0.70 to 1.5 ml, preferably about 0.93 ml
Add water to achieve about 1 Liter total volume (approximately 985 ml water plus dry ingredients = 1 liter).

It should be noted that, as used in this specification and appended claims, the singular forms "a," "an," and "the" include plural referents unless the content clearly dictates otherwise. Thus, for example, reference to a liquid vehicle formulation containing "an ingredient" includes a mixture of two or more ingredients. For further example, reference to a "vehicle" or "embodiment" should also include reference to more than one vehicle, or more than one embodiment, respectively. It should also be noted that the term "or" is generally employed in its sense including "and/or" unless the content clearly dictates otherwise.

The invention has been described with reference to various specific and preferred embodiments and techniques. However, it should be understood that many variations and modifications may be made while remaining within the spirit and scope of the invention as set forth in the claims. For example, one skilled in the art will understand that the volumes of the liquid dilution vehicles, neutral liquid vehicles, and contrast agent mixtures administered, and the concentrations of the iodinated contrast agent may be varied within the scope of the invention.

I claim:

1. A liquid vehicle for enterography examination comprising:
   a solution for oral administration prior to the enterography examination by computed tomography imaging or magnetic resonance imaging, wherein the solution comprises (a) water; (b) about 3 grams/liter to about 8 grams/liter mannitol; (c) about 9.5 grams/liter to about 19.5 grams/liter sorbitol; (d) a viscosity agent including about 0.0001 grams/liter to about 8 grams/liter hydrocolloid gum in an amount such that the viscosity of the liquid vehicle is between 1 to 100 cps, (e) an additional sweetener, and (f) a buffering agent that maintains the pH of the solution within the range of about 2.5 to about 7, wherein the solution does not comprise a barium-sulfate contrast agent, oral administration of the solution distends the small bowel lumen, and the solution retains water in the small bowel lumen during the enterography examination sufficient to maintain a distention of the small bowel lumen to obtain visualization and differentiation of the small bowel lumen from adjacent structures by the computed tomography or magnetic resonance imaging.

2. The liquid vehicle of claim 1, further comprising a nonionic oral contrast agent.

3. A liquid vehicle of claim 1, wherein the solution comprises:
Xanthan Gum—about 0.30 to 1.20 g;
Sodium Hexametaphosphate—about 0.5 to 1.5 g;
Sodium Benzoate—about 0.05 to 0.25 g;
Potassium Sorbate—about 0.05 to 0.15 g;
Calcium Disodium EDTA— about 0.01 to 0.04 g;
Sucralose—about 0.05 to 0.15 g;
Acesulfame Potassium about 0.020 to 0.070 g;
Mannitol—about 3.0 g to 5.00 g;
Citric Acid—about 1.0 to 2.0 g;
Sodium Citrate—about 0.05 to 0.30 g;
Malic Acid—about 0.05 to 0.15 g;
Liquid Flavor—about 0.70 to 1.5 ml; and
sufficient water to achieve at least about 1 liter total volume.

4. The liquid vehicle of claim 3, further comprising a nonionic oral contrast agent.

5. A method for orally administering a nonionic iodinated contrast agent to a patient for CT scanning of the abdomen/pelvis comprising the steps of:
(a) mixing a quantity of the liquid dilution vehicle of claim 1 with an iodinated contrast agent to form a first contrast agent mixture; and
(b) administering the first contrast agent mixture to the patient by having the patient orally consume the contrast agent mixture.

6. The method of claim 5, wherein the iodinated contrast agent is iohexol and the iodine concentration in the contrast agent mixture is between about 6,500 mg/l and about 14,400 mg/l.

7. A method for orally administering a liquid vehicle as defined in claim 1 to a patient prior to CT scanning of the abdomen/pelvis, wherein the liquid vehicle is a neutral HU liquid vehicle, comprising the steps of:
(a) preparing first, second and optionally third quantities of the neutral HU liquid vehicle;
(b) administering the first quantity of the neutral HU liquid vehicle to the patient by having the patient orally consume the first quantity of the neutral HU liquid vehicle over a first period of about 20 minutes;
(c) administering the second quantity of the neutral HU liquid vehicle to the patient by having the patient orally consume the second quantity of the neutral HU liquid vehicle over a second period of about 20 minutes;
(d) after the patient consumes the second quantity of the neutral HU liquid vehicle, administering further liquid volume to the patient by having the patient orally consume over a period of about 20 minutes one of (i) the third quantity of the neutral HU liquid vehicle or (ii) a quantity of water; and
(e) performing a CT scan about 60 to about 70 minutes after the patient begins oral administration of the neutral HU liquid vehicle and obtaining visualization and differentiation of the small bowel lumen from adjacent structures by the CT scan.

8. The method of claim 7, wherein the volume of neutral HU liquid vehicle comprising the first quantity, the second quantity, and third quantity is at least about 500 mL per quantity.

9. The liquid vehicle of claim 1, wherein the solution comprises about 5 grams/liter to about 7 grams/liter mannitol and about 14 to about 18 grams/liter sorbitol.

10. The liquid vehicle of claim 1, wherein the viscosity of the liquid vehicle is between 1 to 50 cps.

11. The liquid vehicle of claim 1, wherein the viscosity of the liquid vehicle is between 1 to 20 cps.

12. The liquid vehicle of claim 1, wherein the solution is configured to be administered to an adult in a volume of at least about 1000 ml such that oral administration of the solution distends the small bowel lumen of the adult, and the solution retains water in the small bowel lumen during the enterography examination sufficient to maintain a distention of the small bowel lumen to obtain visualization and differentiation of the small bowel lumen from adjacent structures by the computed tomography or magnetic resonance imaging.

13. The liquid vehicle of claim 1, wherein the solution does not comprise an iodine-based contrast agent.

14. The liquid vehicle of claim 12, wherein the hydrocolloid gum includes about 0.3 grams/liter to about 1.2 grams/liter xanthan gum.

15. The liquid vehicle of claim 14, wherein the buffering agent includes about 0.1 grams/liter to about 4 grams/liter of an acid.

16. The liquid vehicle of claim 15, wherein the buffering agent includes one or more of (i) about 1 gram/liter to about 2 grams/liter citric acid, (ii) about 0.05 grams/liter to about 0.3 grams/liter sodium citrate, and (iii) about 0.05 grams/liter to about 0.15 grams/liter malic acid.

17. The liquid vehicle of claim 15, wherein the additional sweetener includes one or more of sucralose, acesulfame potassium, aspartame, saccharin, sodium saccharin, *stevia*, neotame, or mixtures thereof.

18. The liquid vehicle of claim 17, wherein the additional sweetener includes one or more of (i) about 0.05 grams/liter to about 0.15 grams/liter sucralose and (ii) about 0.02 grams/liter to about 0.07 grams/liter acesulfame potassium.

19. The liquid vehicle of claim 17, further comprising a bitterness blocker.

20. The liquid vehicle of claim 19, further comprising a preservative including one or more of sodium benzoate, potassium sorbate, sodium hexametaphosphate, calcium disodium EDTA, or mixture thereof.

21. The liquid vehicle of claim 20, wherein the preservative includes one or more of (i) about 0.5 grams/liter to about 1.5 grams/liter sodium hexametaphosphate, (ii) about 0.05 grams/liter to about 0.25 grams/liter sodium benzoate, (iii) about 0.05 grams/liter to about 0.15 grams/liter potassium sorbate, (iv) about 0.01 grams/liter to about 0.04 grams/liter calcium disodium EDTA.

22. The liquid vehicle of claim 20, further comprising about 0.7 to about 1.5 ml/l liquid flavor.

\* \* \* \* \*

UNITED STATES PATENT AND TRADEMARK OFFICE
CERTIFICATE OF CORRECTION

PATENT NO. : 11,529,429 B2  
APPLICATION NO. : 15/450507  
DATED : December 20, 2022  
INVENTOR(S) : Peter Quagliano Page 1 of 1

It is certified that error appears in the above-identified patent and that said Letters Patent is hereby corrected as shown below:

On the Title Page

Item (73) "BEEKLY CORPORATION, Bristol, CT (US)" is deleted.

Signed and Sealed this
Eighth Day of April, 2025

Coke Morgan Stewart
*Acting Director of the United States Patent and Trademark Office*